(12) United States Patent
Hoshizaki et al.

(10) Patent No.: US 7,599,060 B2
(45) Date of Patent: *Oct. 6, 2009

(54) OPTICAL SCANNING CONFIGURATIONS, SYSTEMS, AND METHODS INVOLVING AT LEAST ONE ACTUATOR FOR SCANNING A SCAN HEAD

(75) Inventors: Jon A. Hoshizaki, Cupertino, CA (US); Howard G. King, Berkeley, CA (US); Johannes P. Sluis, Redwood City, CA (US); Steven J. Boege, San Mateo, CA (US); Mark F. Oldham, Los Gatos, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/222,820

(22) Filed: Aug. 18, 2008

(65) Prior Publication Data

US 2008/0316482 A1    Dec. 25, 2008

Related U.S. Application Data

(63) Continuation of application No. 11/265,110, filed on Nov. 3, 2005, now Pat. No. 7,423,750, which is a continuation-in-part of application No. 10/981,440, filed on Nov. 4, 2004, which is a continuation-in-part of application No. 10/440,719, filed on May 19, 2003, now Pat. No. 7,387,891, which is a continuation-in-part of application No. 10/216,620, filed on Aug. 9, 2002, now Pat. No. 7,008,789, which is a continuation of application No. 09/700,536, filed as application No. PCT/US99/11088 on May 17, 1999, now Pat. No. 6,818,437.

(51) Int. Cl.
*G01N 21/64* (2006.01)

(52) U.S. Cl. .............. 356/317; 250/458.1; 422/82.08; 435/288.7; 436/172

(58) Field of Classification Search .............. 356/317, 356/318, 417; 250/458.1, 459.1, 461.1, 461.2
See application file for complete search history.

(56) References Cited

U.S. PATENT DOCUMENTS 4,284,897 A    8/1981    Sawamura et al.

(Continued)

FOREIGN PATENT DOCUMENTS

DE    3441179    11/1984

(Continued)

OTHER PUBLICATIONS

Wittwer, C.T., et al, "The LightCycler™: A Microvolume Multisample Fluorimeter with Rapid Temperature Control," BioTechniques, Vol. 22, No. 1, pp. 176-181 (Jan. 1997).

(Continued)

*Primary Examiner*—F. L Evans
(74) *Attorney, Agent, or Firm*—Mark Feldstein

(57) ABSTRACT

An optical system includes a sample substrate having a surface, the surface defining a 2-dimensional sample plane. The system includes an excitation source configured to provide excitation light to the sample substrate. The system further includes an optical detector configured to receive emission light from the sample substrate and generate detection data. The system also includes a scan head configured at least (i) to direct the excitation light towards the sample substrate, (ii) to receive emission light from the sample substrate and direct the emission light towards the optical detector, and (iii) for scanning relative to the sample substrate. The system includes at least one actuator configured to scan the scan head relative to the sample substrate, the at least one actuator being configured to provide at least one of (1) a relative linear motion and a relative angular motion about a rotational axis generally perpendicular to the sample plane and (2) two relative angular motions about two respectively different rotational axes generally perpendicular to the sample plane.

22 Claims, 11 Drawing Sheets

U.S. PATENT DOCUMENTS

| | | |
|---|---|---|
| 4,626,684 A | 12/1986 | Landa |
| 4,643,877 A | 2/1987 | Opitz et al. |
| 4,673,289 A | 6/1987 | Gaucher |
| 4,683,202 A | 7/1987 | Mullins |
| 4,762,420 A | 8/1988 | Bowley |
| 5,073,029 A | 12/1991 | Eberly et al. |
| 5,091,652 A | 2/1992 | Mathies et al. |
| 5,166,800 A | 11/1992 | Mori et al. |
| 5,169,601 A | 12/1992 | Ohta et al. |
| 5,215,883 A | 6/1993 | Chu |
| 5,243,540 A | 9/1993 | Van Albert et al. |
| 5,256,880 A | 10/1993 | Loree et al. |
| 5,315,375 A | 5/1994 | Allen |
| 5,355,215 A | 10/1994 | Schroeder et al. |
| 5,371,016 A | 12/1994 | Berndt |
| 5,383,023 A | 1/1995 | Walleczek |
| 5,389,544 A | 2/1995 | Sugata et al. |
| 5,459,325 A | 10/1995 | Hueton et al. |
| 5,475,610 A | 12/1995 | Atwood et al. |
| 5,496,517 A | 3/1996 | Pfost et al. |
| 5,547,849 A | 8/1996 | Baer et al. |
| 5,557,398 A | 9/1996 | Wechsler et al. |
| 5,567,947 A | 10/1996 | Kebabian |
| 5,595,708 A | 1/1997 | Berndt |
| 5,656,493 A | 8/1997 | Mullis et al. |
| 5,672,880 A | 9/1997 | Kain |
| 5,736,333 A | 4/1998 | Livak et al. |
| 5,759,781 A | 6/1998 | Ward et al. |
| 5,766,889 A | 6/1998 | Atwood |
| 5,779,978 A | 7/1998 | Hartmann et al. |
| 5,792,610 A | 8/1998 | Witney et al. |
| 5,846,842 A | 12/1998 | Herron et al. |
| 5,854,684 A | 12/1998 | Stabile et al. |
| 5,863,502 A | 1/1999 | Southgate et al. |
| 5,872,623 A | 2/1999 | Stabile et al. |
| 5,926,271 A | 7/1999 | Couderc et al. |
| 5,943,129 A | 8/1999 | Hoyt et al. |
| 6,040,940 A | 3/2000 | Kawasaki |
| 6,057,114 A | 5/2000 | Akong et al. |
| 6,096,272 A | 8/2000 | Clark et al. |
| 6,197,575 B1 | 3/2001 | Griffith et al. |
| 6,211,989 B1 | 4/2001 | Wulf et al. |
| 6,287,871 B1 | 9/2001 | Herron et al. |
| 6,309,601 B1 | 10/2001 | Juncosa et al. |
| 6,331,438 B1 | 12/2001 | Aylott et al. |
| 6,331,441 B1 | 12/2001 | Baich et al. |
| 6,337,740 B1 | 1/2002 | Parce |
| 6,352,672 B1 | 3/2002 | Mabile et al. |
| 6,353,475 B1 | 3/2002 | Jensen et al. |
| 6,364,516 B1 | 4/2002 | Li et al. |
| 6,377,342 B1 | 4/2002 | Coeurveille |
| 6,388,788 B1 | 5/2002 | Harris et al. |
| 6,411,835 B1 | 6/2002 | Modell et al. |
| 6,519,032 B1 | 2/2003 | Kuebler et al. |
| 6,529,275 B2 | 3/2003 | Amirkhanian et al. |
| 6,563,581 B1 | 5/2003 | Oldham et al. |
| 6,563,584 B1 | 5/2003 | Yurino et al. |
| 6,620,623 B1 | 9/2003 | Yershov et al. |
| 6,650,411 B2 | 11/2003 | Odoy et al. |
| 6,818,437 B1 | 11/2004 | Gambini et al. |
| 7,423,750 B2 * | 9/2008 | Hoshizaki et al. ........... 356/317 |
| 2001/0033374 A1 | 10/2001 | Hoyt |
| 2002/0055178 A1 | 5/2002 | Wardlaw |
| 2002/0056804 A1 | 5/2002 | Konagaya |
| 2002/0060791 A1 | 5/2002 | Stumbo et al. |
| 2002/0146688 A1 | 10/2002 | Kinjo |
| 2004/0009586 A1 | 1/2004 | Oldham et al. |
| 2004/0207532 A1 | 10/2004 | Smithson |

FOREIGN PATENT DOCUMENTS

| | | |
|---|---|---|
| DE | 19925161 | 6/1999 |
| EP | 0 065 409 | 11/1982 |
| EP | 0 622 455 | 11/1994 |
| EP | 0 640 828 | 1/1995 |
| EP | 0 987 539 | 3/2000 |
| EP | 1 447 710 A | 8/2004 |
| JP | 07-120392 | 5/1995 |
| JP | 07-120393 | 5/1995 |
| JP | 07-174701 | 7/1995 |
| JP | 08-271521 | 10/1996 |
| JP | 09-281078 | 10/1997 |
| JP | 11-271227 | 10/1999 |
| JP | 2000-121559 | 4/2000 |
| JP | 2001-108684 | 4/2001 |
| WO | WO 95/30139 | 11/1995 |
| WO | WO 97/23649 | 7/1997 |
| WO | WO 97/46707 | 11/1997 |
| WO | WO 98/53301 | 11/1998 |
| WO | WO 99/12008 | 3/1999 |
| WO | WO 99/60381 | 11/1999 |
| WO | WO 00/31518 | 6/2000 |
| WO | WO 00/58715 | 10/2000 |
| WO | WO 01/13096 | 2/2001 |
| WO | WO 01/35079 | 5/2001 |
| WO | WO01/35079 A1 | 5/2001 |
| WO | WO 2004/074820 | 9/2004 |

OTHER PUBLICATIONS

Higuchi et al., "Kinetic PCR Analysis: Real-Time Monitoring of DNA Amplification Reactions," Bio Technology, vol. 11, pp. 1026-1030 (1993).

Ririe et al., "Product Differentiation By Analysis of DNA Melting Curves During the Polymerase Chain Reaction," Analytical Biochemistry, vol. 245, pp. 154-160 (1997).

H.W. Sands Corp., "OLED Emitters Selected by Color Emission," http://www.hwsands.com/productlists/oled_emitters_color_emission.htm (printed Jan. 10, 2003).

Hebner et al., "Local Tuning of Organic Light-Emitting Diode Color by Dye Droplet Application," American Institute of Physics (1998).

Qiu et al., "Room Temperature Ultraviolet Emission From an Organic Light-Emitting Diode," American Institute of Physics (2001).

Teresko, "Winning Technologies: Organic Light Emitting Diode," Industry Week (Dec. 11, 2000).

Tollefsrud, "Electronic Paper: Organic Light Emitting Diode," http://komar.cs.stthomas.edu/gm425/01s/Tollefsrud2.htm (printed Jan. 10, 2003).

International Search Report, mailed Dec. 8, 2003, for International Application No. PCT/US03/15945.

International Search Report issued in PCT/US2005/039839. May 19, 2006.

Patent Abstract of Japan, JP 06-045654A, vol. 018, No. 270, May 23, 1994, Eastman Kodak Japan KK.

* cited by examiner

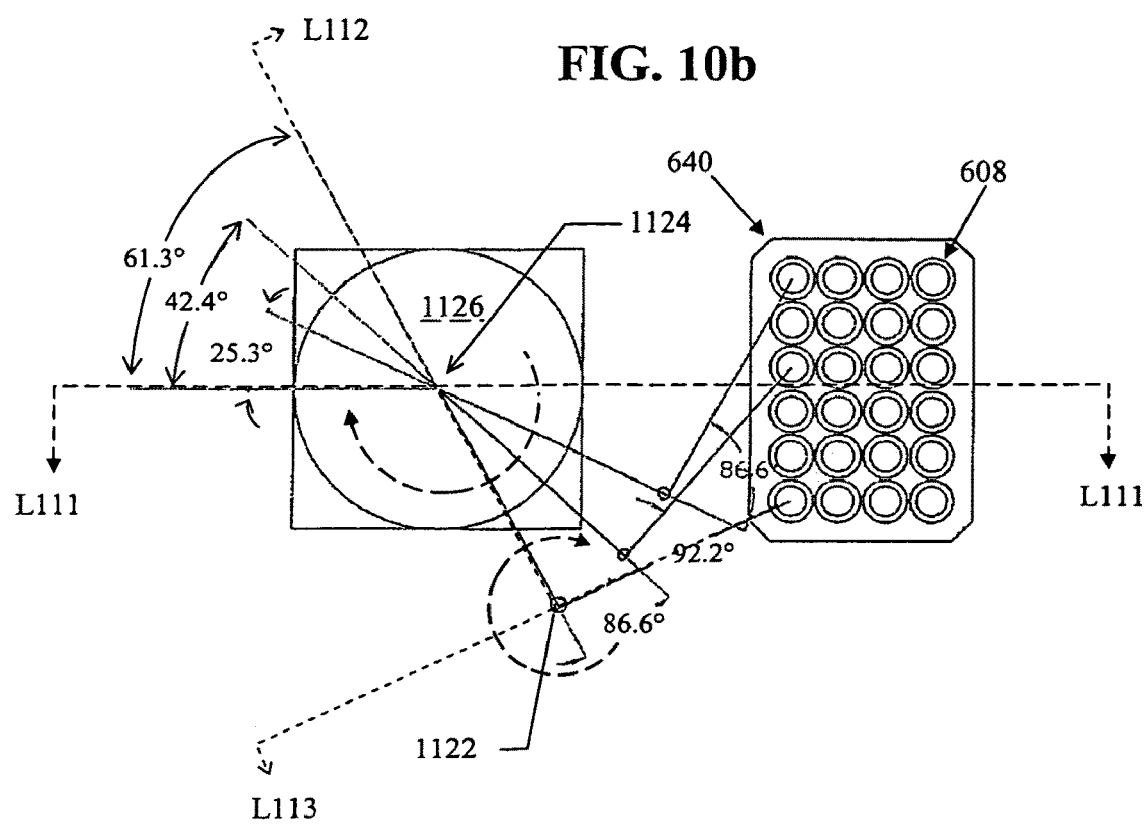

OPTICAL SCANNING CONFIGURATIONS, SYSTEMS, AND METHODS INVOLVING AT LEAST ONE ACTUATOR FOR SCANNING A SCAN HEAD

I. CROSS-REFERENCES TO RELATED APPLICATIONS

The present application is a continuation of co-pending application Ser. No. 11/265,110, filed on Nov. 3, 2005, which is a continuation-in-part of co-pending U.S. patent application Ser. No. 10/981,440 filed on Nov. 4, 2004, which in turn is a continuation-in-part of co-pending U.S. patent application Ser. No. 10/440,719, filed May 19, 2003, which in turn is a continuation-in-part of co-pending U.S. patent application Ser. No. 10/216,620, filed Aug. 9, 2002, which in turn is a continuation of co-pending U.S. patent application Ser. No. 09/700,536, filed Nov. 29, 2001, which claims priority to PCT/US99/11088, filed May 17, 1999, which published as publication number WO 99/60381 on Nov. 25, 1999, all of which are incorporated herein in their entireties by reference.

Cross-reference is made to co-pending U.S. patent application Ser. No. 10/440,920 entitled "Optical Instrument Including Excitation Source" to Boege et al., co-pending U.S. patent application Ser. No. 10/440,852 entitled "Apparatus And Method For Differentiating Multiple Fluorescence Signals By Excitation Wavelength" to King et al., both filed on May 19, 2003, and U.S. patent application Ser. No. 10/735,339, filed Dec. 12, 2003, Reexamination Control No. 90/007,275, filed, Oct. 29, 2004, for U.S. Pat. No. 6,211,989, including U.S. Pat. No. 6,211,989, all of which are incorporated herein in their entireties by reference.

II. FIELD

This invention relates to methods and optical systems for optical scanning of a target sample, including systems having low mass optical scan heads. The present invention also relates to methods and systems for performing sample assays, and for producing and measuring optical responses and signatures.

III. BACKGROUND

A Light-Emitting Diode (LED) can be an excitation source for optically transduced assays, such as fluorescent measurements. The need for providing an LED excitation beam source that does not exhibit excitation beam intensity changes and/or an excitation beam spectral shift has not been satisfied. A device compatible with nucleotide amplification reactions, detecting such reactions, and capable of processing a relatively large number of amplification reactions is desirable. A device capable of providing enhanced scanning, such as enhanced scanning speed and enhanced scanning methods, of multiple reactions or samples is also desirable.

IV. SUMMARY

According to various embodiments, a system and a method configured to provide optical scanning or interrogation of a sample substrate is provided where the system is thermally compensated. Thermal compensation may be, passive, active, or both.

Various embodiments of the invention comprise an optical system and method having at least one LED configured to provide excitation light to the sample substrate. The temperature of the LED may, for example, be thermally stabilized. As another example, detected data may be adjusted to compensate for temperature-dependent changes in the LED excitation light, such as changes in its intensity or spectrum.

Various embodiments of the invention comprise an optical system and method using a scanning configuration for scanning an optical scan head relative to a sample substrate based at least relative linear motion, a relative linear motion and a relative angular motion, two relative angular motions, or any combination thereof.

Various embodiments of the invention comprise an optical system and method having a low mass scan head for scanning a sample substrate. A low mass scan head can, for example, contain a limited number of components such that its inertial mass can be reduced and its potential acceleration and velocity increased.

V. BRIEF DESCRIPTION OF THE DRAWINGS

Various embodiments of the present teachings are exemplified in the accompanying drawings. The teachings are not limited to the embodiments depicted in the drawings, and include equivalent structures and methods as set forth in the following description and as would be known to those of ordinary skill in the art in view of the present teachings. In the drawings.

Figure 1:
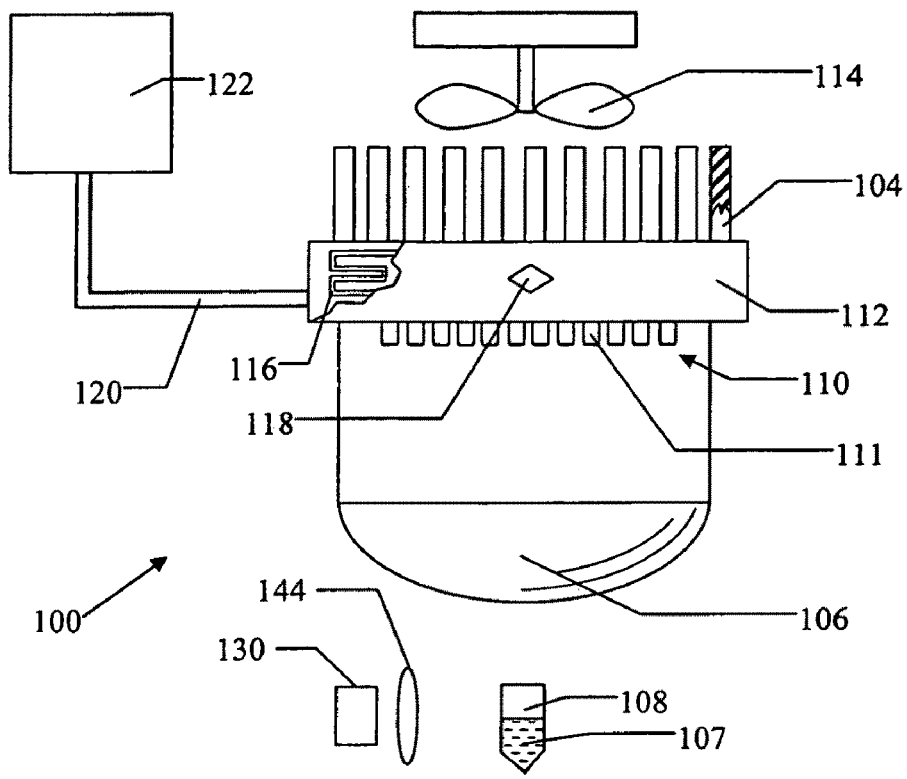
FIG. 1 is a side view in partial cross-section of a system including a heater providing temperature stabilization for an LED array according to various embodiments.

It is to be understood that both the foregoing general description and the following detailed description are exemplary and explanatory only and are intended to provide a further explanation of the various embodiments of the present teachings. The various prophetic examples (i.e., "Example 1," "Example 2", etc.) and headings associated therewith, are provided to illustrate various embodiments and aspects of the present disclosure. Such examples are intended to be considered within the scope of the present disclosure as a whole, and aspects of one example may be combined with another, according to various embodiments.

VI. DESCRIPTION OF CERTAIN EMBODIMENTS OF THE INVENTION

Reference will now be made in detail to certain embodiments of the invention, examples of which are illustrated in the accompanying drawings. Wherever possible, the same reference numbers will be used throughout the drawings to refer to the same or like parts.

The section headings used herein are for organizational purposes only, and are not to be construed as limiting the subject matter described.

All documents cited in this application, including, but not limited to patents, patent applications, articles, books, and treatises, are expressly incorporated by reference in their entirety for any purpose.

Indefinite articles "a" and "an" carry the meaning of "one or more" in open-ended descriptions, such as those containing the transitional phrase "comprising."

According to certain embodiments, the present invention provides optical systems configured to provide optical scanning or interrogation of a sample substrate. The system can be actively thermally compensated, passively thermally compensated, or both. Optical systems according to certain embodiments comprise at least a sample substrate, an LED, an optical detector, a temperature dependent unit, an optional temperature sensor, and an active or passive temperature compensation system or both. According to these embodiments, the LED is configured to provide excitation light to the sample substrate. The optical detector is configured to receive emission light from the sample substrate and generate detection data. Systems according to the present invention may, in various embodiments, comprise more than one of a recited element, such as, for example, multiple LEDs, multiple optical detectors, multiple filters, or multiple temperature sensors, except as specified to the contrary.

According to various embodiments, a system can comprise one or more LEDs, photodiodes, operational amplifiers, and LED-current control circuits. Such components may have temperature dependent properties, meaning that their properties (e.g., LED intensity) can change with temperature variations. A temperature compensation system can, for example, maintain some or all of these components at a constant temperature to eliminate or reduce changes in the temperature dependent property or properties. The constant temperature can be, according to certain embodiments, elevated from an ambient temperature. The constant temperature can be, according to certain embodiments, lower than an ambient temperature. Similarly, the constant temperature may be at or near ambient, according to certain embodiments. For example, the system components can be held at a constant temperature above an ambient temperature using a resistive heating element as a heat source under the control of the temperature compensation system. As an additional example of temperature compensation, a temperature compensation system can also adjust detection data to compensate for the effects of temperature changes. As other examples, a temperature compensation system can distribute thermal energy, provide thermal insulation or buffering, or any combination thereof.

According to certain embodiments, the temperature dependent unit ("TDU") will include the LED, the optical detector, or both, as well as optionally other elements. The TDU may also consist or consist essentially of the LED, the optical detector, or both. Thus, according to certain embodiments, the TDU may be coextensive with its components, such as an LED. That is, the TDU is not necessarily an element distinct from other specified elements of the system. Rather, it can be, according to certain embodiments, a designation for other specified components whose temperature is to be monitored, controlled, regulated, or otherwise compensated. Additionally, however, the TDU may also comprise additional functional elements, such as circuitry, support elements (e.g., a housing or support substrate, thermal control elements, and combinations thereof).

As used herein, a "sample substrate" refers to a substrate or plate, such as a plate containing wells or microwells used for chemical or biological assays or screenings, that contains or is configured to contain one or more samples to be optically examined. The samples may be contained, for example, on a surface, in a volume (such as a microwell), or in a capillary. The sample substrate may also include or be associated with a thermal cycler block to provide thermal control over the sample, such as for thermal cycling used in PCR application.

Sample substrates can include or contain, for example, regions for performing chemical and/or biochemical assays or screenings, where the assays or screenings include a mechanism for optically transduced measurement. The sample substrate can also be referred to as the illumination target, or just "target," as provided in U.S. Pat. No. 6,744,502 by Hoff and Oldham, which is hereby incorporated by reference in its entirety.

The mechanism for optical transduction of the assay property or result may be fluorescent tags, as just one example. As another example, the optically transduced measurement may be based on optical absorption, reflection, other spectroscopic responses, or any combination of spectroscopic measurements. It may also entail temporally static measurements, time resolved measurements, or both. As further examples, the measurement can entail a spectrally resolved or frequency domain measurement, such as a Fourier transform method. As a still further example, it may entail non-linear measurements, such as Raman and multi-photon processes.

"Optical detector" refers to devices that convert electromagnetic energy into an electrical signal, and include both single element and multi-element or array optical detectors. Thus optical detectors are devices capable of monitoring an electro-magnetic (e.g., optical) signal and providing an electrical output signal or data related to the monitored electromagnetic (e.g., optical) signal. Such devices include, for example, photodiodes, including avalanche photodiodes, phototransistors, photoconductive detectors, linear sensor arrays, CCD detectors, CMOS optical detectors (including CMOS array detectors), photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrating circuit. Suitable pre-preamplifiers include integrating, transimpedance, and current gain (current mirror) pre-amplifiers.

The term "temperature dependent property" is used herein to refer to the property of a device or device element that is affected by temperature. The temperature of the device or element is, of course, fundamentally a temperature dependent property of the device or element. The temperature dependent property may be monitored, according to certain embodiments, using an absolute scale, such as degrees Celsius, or as a relative value compared to, for example, a set point or baseline value.

For example, according to certain embodiments, a temperature dependent property may be one or more of a temperature, a temperature dependent optical property, a temperature dependent electronic property, a temperature sensor signal or response, or any combination thereof.

According to certain embodiments, the temperature dependent property may be, for example, an electrical property, such as resistance, that is affected by temperature directly or indirectly. Thus, as one example, the device (e.g., a temperature dependent unit) may comprise an LED and the resistance of the LED (if temperature dependent) would be a temperature dependent property of the LED and of the device comprising the LED. Other electronic components, such as optical detectors, including photodiodes, and amplifiers may also have temperature dependent electrical properties that can be monitored. For example, resistive elements in transimpedance amplifiers may have temperature dependent electrical properties that can be monitored.

The temperature dependent property may also include properties that are a derived or indirect function of a temperature dependent property. Thus, for example, if electrical resistance is a temperature dependent property, current or voltage, which would be functions of the resistance, could also be temperature dependent properties. Other temperature dependent properties may include, for example, temperature dependent properties of an optical detector, such as a photodiode. For example, the "dark current" or noise of a detector may be temperature dependent. Temperature sensors may thus include electronic circuits and signal measurement devices or elements configured to monitor, for example, dark current or noise.

In addition to the exemplary electrical properties, temperature dependent properties may include optical properties of optically active components, such as excitation sources and optical detectors. For example, for a conventional LED the intensity and spectrum of its optical output may both be temperature dependent properties of the LED. For commercial LEDs, such temperature dependence is usually well characterized. As another example, the amplitude and range of sensitivity and response of the optical detector may also be temperature dependent. Temperature sensors may thus include optical detectors.

A "thermal control signal" is understood to mean a signal that is used or can be used to provide thermal control to a device. For example, it may be the output of a temperature sensor. Such a thermal control signal may be unprocessed or processed, including unamplified or amplified. For example, a signal may be processed in a computer or designated circuit, and a resultant derived or calculated signal can be used to provide thermal control. The resultant derived or calculated signal would also be considered a thermal control signal.

The thermal control signal may be used, for example, to adjust the power to a thermal control device, such as a heater or cooler, as discussed elsewhere herein. The thermal control signal may also be used, for example, to scale or compensate data to normalize variations due to temperature changes, as also discussed elsewhere herein.

A "temperature compensation system" is used herein to refer to any system that can compensate for temperature changes. It may include, for example, "active" thermal compensators that can actively add or remove thermal energy. It may also include "passive" thermal compensators that insulate or buffer temperature changes.

For example, a temperature compensation system may include an active thermal compensation system that actively adjusts the properties of a device to counter balance or offset other thermal changes. Thus, it may include, for example, a system designed to maintain a constant output intensity of an LED by, for example, adjusting the applied current or voltage to compensate for intensity changes caused by temperature variations. As another example, to counter balance or offset other thermal changes the LED duty cycle may be adjusted to maintain as constant the optical flux, integrated over a given time period. Thus, the LED output can be actively maintained at a constant, or relatively constant, level by compensating for changes in temperature with changes to the operating current or other control parameters (e.g., duty cycle). An active temperature compensation system may also include systems that scale or adjust data values to normalize variations due to temperature effects, as discussed further below in the context of temperature compensated detection data.

Other temperature dependent properties and thermal control signals may also be used for active thermal compensation systems. Similarly, other scaling or normalizing techniques may be used, and may depend on a known or empirically derived relationship between the raw detection data and the temperature dependent property.

The term "regulate," as used in the context of "configured to regulate," means that the system, device, or element so configured has the functionality to regulate a given property or function. Being "configured to regulate" a given property or function does not require that the system, device, or element is necessarily always actively regulating the property or function. Further, the regulation can be direct or indirect. For example, the thermal control signal configured to regulate an operating temperature may be processed or converted prior to transmission to the regulating system.

"Detection data" refers to data derived from or related to the optically transduced assay measurement. Thus the detection data may be the output signal from an optical detector configured to receive emission light from a sample substrate. It may also include such signals that are further processed, by, for example, A to D conversion, amplitude scaling, offset adjustment, frequency modulation or demodulation, or other signal processing techniques.

"Temperature compensated detection data" refers to detection data that has been processed or otherwise scaled to compensate for changes in temperature of one or more elements of the optical system. For example, if the temperature and LED intensity vary during the course of a fluorescence-based measurement, the measured fluorescent emission intensity (detection data) will be a function not only of the sample properties (e.g., fluorescent probe concentration), but also a function of the LED intensity. Hence, the measured fluorescent intensity will be a function of temperature, and this can lead to undesirable inaccuracies in the data. However, if the LED intensity (or a property correlated therewith) is monitored, the data can be scaled based on this intensity.

For example, if the LED intensity decreases with increasing temperature, causing a subsequent decrease in sample emission intensity, the temperature compensated detection data may have its amplitude scaled (in this case increased) to compensate for decreases in the LED intensity. Similarly, increases in LED intensity can be compensated for by scaling, to reduce, the amplitude of the detected data. One exemplary scaling method would be to take the ratio of the raw fluorescent intensity to the thermally dependent LED intensity or a correlated property (e.g., fluorescent intensity/LED intensity), to normalize LED intensity variations where the fluorescent intensity is linearly related to the LED intensity. Another exemplary scaling method entails using a temperature dependent signal gain system, where the temperature dependence of the signal gain system has the same absolute value but opposite sign as the temperature coefficient being compensated (e.g., the LED output intensity temperature coefficient). The resultant scaled or normalized data would be temperature compensated detection data, which is discussed further below.

As another example, if the background signal or "dark current" of a detector increases with increasing temperatures of the detector, a temperature dependent offset may be subtracted from the detection data to remove temperature effects. Functionally, the purpose of temperature compensated detection data is to provide a data output where the effects of temperature changes have been minimized or eliminated, as much as possible.

Active Temperature Compensation Systems and Methods

As part of an active temperature compensation system, a temperature sensor can be present and be configured to provide at least two functions. First, the temperature sensor can be configured to monitor at least one temperature dependent property of the TDU. Second, the temperature sensor can be configured to generate a thermal control signal related to the at least one temperature dependent property.

According to certain embodiments, an active temperature compensation system and method may include passive temperature compensation components, such as those discussed elsewhere herein. Such passive components can be used either passively (e.g., a cooling fan that is always on) or actively (e.g., a cooling fan that is actively controlled), depending on the embodiment.

The temperature sensor can be used to measure directly, indirectly, or by calculation, the temperature of the system components. The temperature sensor can be configured according to various embodiments to measure an operating temperature for various components of the system. The temperature sensor can provide feedback to a temperature regulating system. The temperature regulating system can monitor the amount of heating or cooling provided by a heat source or a heat sink to maintain the system components at a nominal temperature within an acceptable deviation value range. The temperature sensor can be used to form thermally compensated detection data. Multiple temperature sensors may also be used to measure, for example, temperature gradients or temperatures of different components or parts of components.

According to certain embodiments, the temperature sensor can be a component of the TDU or in thermal contact with the TDU. Additionally, according to other embodiments, the temperature sensor need not be in thermal contact with the TDU. The temperature sensor can alternately or additionally monitor the TDU temperature, according to certain embodiments, by monitoring a temperature dependent property of the TDU. For example, in embodiments where the LED is part of the TDU, the temperature sensor can remotely (i.e., non-contact) monitor a temperature dependent optical property of the LED. As another example, an optical response of the optical detector can be monitored, where such a response (e.g., gain) is temperature dependent and the optical detector is part of the TDU.

For example, according to certain embodiments, a temperature sensor can be configured to monitor at least one temperature dependent optical property of the temperature dependent unit. For instance, an LED can be a component of the TDU and a temperature sensor can be configured to monitor at least one temperature dependent property of the LED. The temperature dependent property of the LED can be, for example, a temperature of the LED, a temperature dependent optical property of the LED, such as an optical output power (emission intensity) or wavelength, or a temperature dependent electrical property, such as resistance. Thus, according to certain embodiments, a temperature sensor may be an optical detector configured to monitor the LED emission. According to certain embodiments, a temperature sensor may also be in thermal contact with the LED or LED array.

According to various embodiments, the TDU can include one or more optical detectors, such as first and second optical detectors. The one or more optical detectors can be based on or include, as one example, one or more photodiodes. According to certain embodiments, a temperature sensor can be configured to monitor at least one temperature dependent property of at least one of the first and second photodiodes. The photodiode temperature dependent property can be, for example, a temperature, a temperature dependent optical property, such as its optical sensitivity, or a temperature dependent electrical property, such as its resistance or dark current.

Example 1

For example, FIG. 1 is side partial cross-sectional view of a system 100 configured for active temperature compensation, according to various embodiments, including an LED array 110 that includes a plurality of LEDs 111. According to certain embodiments, a single LED may be used, in which element 110 would be a single LED. When multiple LEDs 111 are present, they may be of a common type (i.e., common spectral properties) or they may be different, and may be operated, for example, simultaneously, sequentially, or any combination thereof. The system can also include a focal lens 106. The focal lens 106 can focus excitation light emitted by the LED array 110. The LED array 110 can be in physical and/or thermal contact with a substrate 112. The LED array 110 can include one or more rows or patterns of individual LEDs. The substrate 112, which can be a printed circuit board (i.e., PCB), can include one or more highly thermally conductive layers that can distribute heat across the substrate. The highly thermally conductive layer may be a copper ground plane layer of a PCB board, or may be an additional layer comprising, for example, aluminum or steel. The highly thermally conducting layer may be, as possible examples, a surface layer in direct contact with the thermal elements (e.g., LED array 110) attached thereto or may be an interlayer of a multilayer substrate. A heating device 116, for example, a resistive heating element, can be provided in thermal contact with the LED array 110. The heating device 116 can be included in, on, or in and on the substrate 112. The system 100 can include a temperature sensor 118 in thermal contact the LED array 110. The temperature sensor can be centrally located with respect to the LED array 110. The temperature sensor 118 can be included on the substrate 112. A temperature regulator or temperature regulating system 122 can be provided that is capable of receiving a signal from the temperature sensor 118. The temperature sensor 118 and temperature regulating system 122 can be integrated and/or can be of a unitary construction. The temperature regulating system 122 can control the heating device 116. The temperature regulating system 122 can control a fan 114. The temperature regulating system 122 can control the fan 114 and the heating device 116. For example, the temperature regulating system 122 can be used to control the heating device 116 to reach or maintain a nominal operating temperature while the fan 114 prevents the operating temperature from getting too high. This optimization can be used, for example, if the LED array 110 is not on continuously. For example, heating device 116 can provide additional heat when some or all of the plurality of LEDS 111 in LED array 110 are not on. The fan 114 can direct an air current over one or more cooling fins 104. The cooling fins 104 can be in thermal contact with the LED array 110, with the substrate 112, or with both. The temperature regulating system 122 can send signals to and/or receive signals from the temperature sensor 118, the heating device 116, and/or the fan 114. The temperature regulating system 122 can send and receive signals using wires 120, or via wireless controllers integrated in or associated with the various components. Excitation light can be emitted from LED array 110 and directed to one or more reaction region 108 on a sample substrate. The reaction region 108 can include a sample 107. The reaction region can be, for example, a well on a microtiter tray. One or more optical signals from the sample 107 may be monitored with a detector without or without additional optical components, such as detector 130 and lens 144. Although the axis between detector 130 and reaction region 108 is generally perpendicular to the axis between LED array 110 and reaction region 108, other configurations, such as a co-axial configuration, may also be used according to certain embodiments.

Example 2

Figure 2:
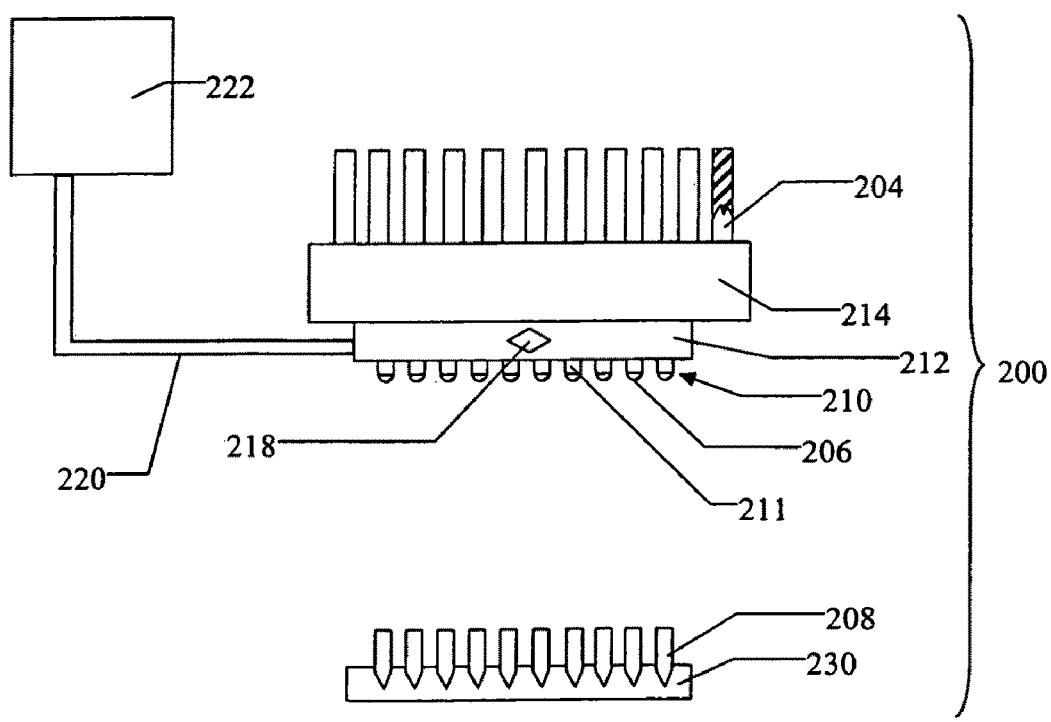
FIG. 2 is a view in partial side cross-section of a system including a thermoelectric device providing temperature stabilization for an LED array according to various embodiments.

FIG. 2 is a side cross-sectional view of a system 200, according to various embodiments, that includes an active temperature stabilization device for an LED array 210, for example, by including a plurality of LEDs 211. A focal lens 206 can be included to focus excitation light emitted from each of the individual LEDs 211. The LED array 210 can be in physical and/or thermal contact with a substrate 212. The system 200 can include a temperature sensor 218 in thermal contact with the LED array 210, the substrate 212, or both. The temperature sensor 218 can be included in or on the substrate 212. A temperature regulating system 222 can receive a signal from the temperature sensor 218. The temperature regulating system 222 can control a thermoelectric device 214, for example, a Peltier device. The thermoelectric device 214 can be in thermal contact with the LED array 210, with substrate 212, or with both. The thermoelectric device 214 can transfer thermal energy from an ambient environment to the LED array 210. The thermoelectric device 214 can transfer thermal energy to an ambient environment from the LED array 210. The thermoelectric device 214 can include a temperature sensor. A plurality of cooling fins 204 can be in thermal contact with the LED array 210 and/or with the thermoelectric device 214. The temperature regulating system 222 can send signals to and/or receive signal from the temperature sensor 218, and/or the thermoelectric device 214, for example, through wires 220. Excitation light can be emitted from LED array 210 and can be directed to a plurality of reaction regions 208, for example, held in a thermal cycling block 230. The thermoelectric device 214 can be used to maintain a lower temperature than could be otherwise achieved under operating conditions. This can permit the LED array 210 to operate more efficiently, with a higher total flux output. The thermoelectric device 214 can be used in a heating mode, for example, to reach or maintain a temperature when the LED array 210 is not on. The thermoelectric device 214 can be used in a cooling mode when the duty cycle of the LED array 210 is high enough to require cooling. According to certain embodiments, there may be a one-to-one correspondence between the number of LEDs 211 and the number of reaction regions 208, as shown. According to other embodiments, there may be a greater number of LEDs than reaction regions, for example as shown in FIG. 1. According to still other embodiments, there may be a fewer number of LEDs than reaction regions. As just one example, there could be three LEDs, each having respectively different optical properties, that are configured to illuminate a single reaction region. As another example, there could be three LEDs, each having respectively different optical properties, that are configured to illuminate multiple reaction region, such as six or more.

Although thermal compensation can be used to maintain as constant the temperature dependent spectral output of an LED, controlled temperature variations may be used control the temperature dependent spectral output of an LED to perform, for example, spectroscopic analyses. For instance, in the case of an LED having a 4.0 nm/° C. coefficient of spectral changes per degree centigrade, a 1 degree temperature change will change the LED output spectrum by 4.0 nm. Thus, by changing the temperature of the LED, such as by ramping or stepped changes, an LED can be used to provide multiple optically distinct ranges of excitation light and can be thus used to make, for example, spectrally dependent measurements, such as an absorption spectral analysis. Such thermally controlled-spectral analysis can be used independently or in conjunction with a thermally compensated system or method to provide additional levels of spectral analysis and discrimination. For example, the LED temperature can be stepped between two different temperature to provide two optically distinct ranges of excitation light, and collected emission can be correlated with the temperature, and hence optically distinct range, to discriminate, for example, between two overlapping optical tags. As another example, the LED temperature could be oscillated, and the emission light can be analyzed based on this frequency, to discriminate again background noise, for example. A phase analysis could also be conducted on the emission light, to measure shifts from the phase of the LED temperature oscillation, to provide a further level of analysis for the emission light. The temperature of the LED may be controlled with the same elements (e.g., heating and cooling elements) discussed herein for use in temperature compensation, as well as any other element functionally capable of applying or removing heat.

Example 3

Figure 3A:
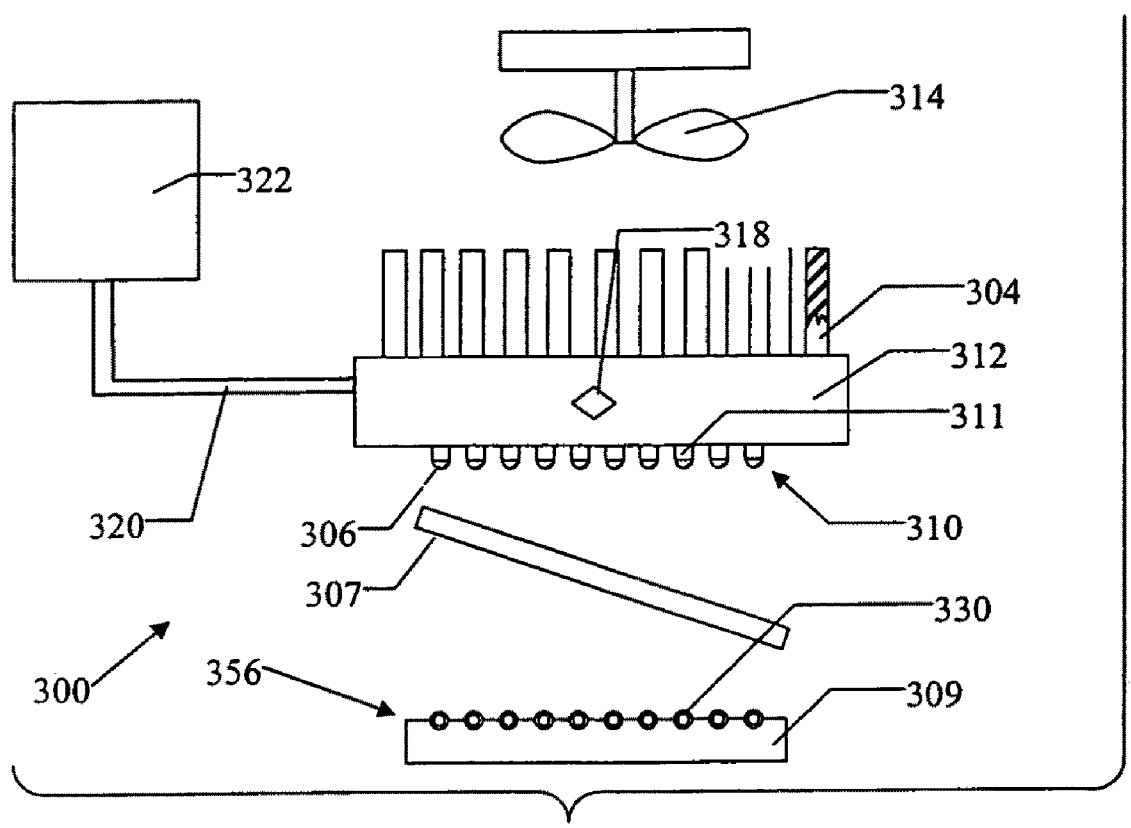
FIG. 3a is a side view in partial side cross-section of a system including a fan and cooling fins providing temperature stabilization for an LED array according to various embodiments.

FIG. 3a is a side cross-sectional view of a system 300 according to various embodiments and capable of providing temperature stabilization for an LED array 310 including a plurality of individual LEDs 311. A focal or collimating lens 306 can be included to focus excitation light emitted from each of the individual LEDs 311. The collimating lens can be a Fresnel lens. A beam splitter 307, which can be a single element as shown or multiple elements, can be included to separate excitation light from emission beams. The beam splitter 307 can be replaced by a filter or beam splitter as described, for example, in U.S. patent application Ser. No. 10/735,339, filed Dec. 12, 2003, which is incorporated herein in its entirety by reference. The LED array 310 can be in contact with a substrate 312. The system 300 can include a temperature sensor 318 in thermal contact with the LED array 310. The temperature sensor 318 can be included in, on, or in and on the substrate 312. A temperature regulating system 322 can receive a signal from the temperature sensor 318. The temperature regulating system 322 can control a fan 314. The fan 314 can direct an air current over a plurality of cooling fins 304. The cooling fins 304 can be in physical and/or thermal contact with the LED array 310. The temperature regulating system 322 can communicate with the temperature sensor 318, and/or the fan, through wires 320. Excitation light can be emitted from LED array 310 and directed to a reaction region 308 formed or disposed in, on, or in and on a substrate 309.

The reaction regions can include capillaries 330 of a capillary array. The capillaries 330 can each have a portion that passes through a detection zone 356.

Figure 3B:
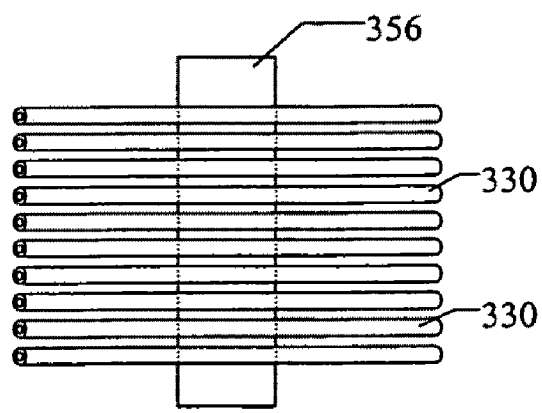
FIG. 3b is a top plan view of a capillary sample holder according to various embodiments.

FIG. 3b is a top plan partial view of the array of capillaries 330 shown in FIG. 3a, and the detection zone 356. The capillaries can traverse the detection zone 356, where excitation light from the LED array 310 (FIG. 3a) can be directed. For example, the excitation light can be used for fluorescence detection of analytes in capillaries of a capillary electrophoresis device. Such can be the case in DNA sequencing and fragment length analysis applications.

Active Temperature Regulation Systems and Methods

According to various embodiments, the active regulation of an operating temperature of the TDU by the temperature compensation system can be in any form capable of, in response to a control signal, adding or withdrawing thermal energy from the TDU to maintain a desired temperature value or range. For example, the temperature compensation system can include elements such as heaters, coolers, or fans, that are in thermal contact with the TDU and that are activated or controlled (directly or indirectly) by the thermal control signal. The temperature control system can include a heater. The system can include a cooler. The system can include both a heater and a cooler. Cooling and heating rates can be augmented by using a plurality of heaters and/or coolers as desired. If a heater is provided, it can comprise a plurality of different types of heating devices. If a cooler is provided, it can comprise a plurality of different types of cooling devices.

As one example, the temperature compensation system can comprise a heating element and control electronics configured, with the temperature sensor, to maintain the TDU at an elevated temperature relative to the ambient temperature. Thus, assuming for this example an ambient temperature of 20° C., the temperature compensation system can be configured to maintain the TDU at a working temperature of 25° C. to some specified degree of precision. If the TDU temperature starts to drop below the set point, as measured by the temperature sensor, the heater output will be, via the thermal control signal, activated or increased to raise (or stop the drop in) the TDU temperature. Similarly, if the TDU temperature starts to rise above the set point, the heater output will be, via the thermal control signal, deactivated or reduced to lower (or stop the rise in) the TDU temperature.

An active temperature compensation system, according to various embodiments, can be configured to regulate the operating temperature of the TDU based on the at least one temperature dependent property and optionally at least one non-temperature dependent property.

The non-temperature dependent property may include, for example, at least one property chosen from an age of the at least one optical component, aging of electrical components, power supply variations, changes in transmission or reflection of optical components such as lenses and filters, altitude and air density effects such as lower heat capacity of air used for heat transfer at higher elevations or lower ambient pressures, an anticipated temperature change, a heat capacity of the TDU, a temperature regulation lag time, and thermal conductivities of materials in the system. Age in this context can be either a real time age (i.e., months since constructed or first operated) or an age in terms of amount of time in actual use.

Optical component age may be a relevant property since, for example, LED emissive intensity may diminish with age independent of temperature. To the extent age-related intensity losses and other non-temperature dependent effects are not appropriately accounted for, these effects may be improperly attributed, in certain systems, to temperature effects, and therefore inappropriately compensated.

An anticipated temperature change may be a relevant property according to certain embodiments. For example, if a heat-generating component (such as a thermal cycle used during PCR, which can entail heating for denaturing, annealing, and extension steps) is anticipated to be activated (or deactivated), it may be desirable to begin to reduce (or increase) the TDU temperature in advance of this event. Similarly, it may be desirable to provide less heat, where added heat is necessary to maintain thermal stability, in advance of the heat generating event.

Heat capacity (thermal mass) of the TDU can be relevant, according to certain embodiments, to provide a scaling factor or magnitude to the temperature regulation. Similarly, thermal resistance can be relevant, according to certain embodiments, to provide a scaling factor or magnitude to the temperature dependent regulation. Thus, for example, for a relatively large TDU heat capacity and/or thermal resistance, the magnitude of the active temperature compensation may be relatively or proportionally large. Further, heat capacity and thermal resistance can be used, according to various embodiments, to adjust the temporal profile of the active temperature compensation. For example, with the thermal equivalent of a large electrical resistive-capacitive (RC) time constant, the magnitude of the active temperature compensation may be relatively or proportionally large at the beginning of a control cycle and lower at later times.

Similarly, if there is a known, expected, or empirically determined lag time for the effects of temperature compensation, this lag time may be accounted for, according to certain embodiments, to avoid over heating or cooling of the TDU. The lag time may be due, for example, to the finite time required to provide or stop heating or cooling from a heating or cooling element.

The regulation of the TDU operating temperature according to certain embodiments, may comprise a feedback control based on at least a difference between a measured value of the at least one temperature dependent property and a desired value of the at least one temperature dependent property. As an example, according to certain embodiments, the temperature sensor may be configured to monitor a rate of change in the at least one temperature dependent property and generate the thermal control signal as a function of the rate of change.

For example, if the desired temperature is 20° C., to some desired degree of precision, the degree or amount of temperature regulation in response to a measured temperature of 30° C. could be greater in a proportional feedback system than that at a measured value of 25° C. As an example of one general equation to express proportional temperature regulation, degree or amount of temperature regulation ("regulative intensity" or "RI") could be defined according to the equation $RI=X(T_D-T_m)^n$, where X is a proportionality constant, $T_D$ is a desired temperature, $T_m$ is a measured temperature, and n is an exponent, such as 1, 2, or 3 (though it could be any appropriate value, including non integers). As another example, proportional integral differential (PID) feedback control may be used. As still another example, a fuzzy logic feedback system may be used. A feedback equation may further take into various considerations, such as start-up or cool down times for the temperature regulating element (e.g., heater), for example, as discussed above.

According to various embodiments, the active temperature compensation system can be configured to maintain the operating temperature within an operating temperature range including a minimum temperature and a maximum temperature separated by, for example, about 15° C., about 5° C., about 1° C., or about 0.5° C. The operating temperature range can also be specified as a nominal temperature (e.g., 20° C.) and an acceptable deviation value or range (e.g., ±1° C. or ±0.5° C.).

According to various embodiments, the active temperature compensation system can include a user input device that is capable of being programmed to maintain an operating temperature range including a minimum temperature and a maximum temperature or a desired temperature and temperature range. The system can include a display capable of displaying the operating temperature of the system.

According to various embodiments, the temperature compensation system can include an error signaling device capable of signaling an alarm when the operating conditions exceed a set point, such as a temperature being greater than a maximum temperature, less than a minimum temperature, or not responding at an expected rate.

According to various embodiments, the temperature sensor can include a thermister, a thermocouple, a resistance temperature detector (RTD), a non-contact temperature sensor, a bandgap semiconductor resistive temperature detector, a platinum resistive temperature detector, a bi-metallic temperature detector, a combination thereof, or the like. Functionally, the temperature sensor is configured to at least monitor the temperature dependent property.

According to various embodiments, a system and method provide for maintaining emission intensity and spectral stability of an LED. The method can comprise: providing a system comprising an LED; generating excitation light with the LED; measuring (directly or indirectly) an operating temperature of the LED; and regulating the operating temperature. The regulation may be by at least one of transferring heat from the LED and transferring heat to the LED, based on the operating temperature, to maintain, for example, the temperature, emission intensity, and/or spectral stability of the LED. The regulating can comprise retrieving from a memory source adjustment data corresponding to a desired operating temperature or temperature range at which emission intensity and spectral stability of the LED are to be maintained.

Illumination Systems and Methods

An LED illumination system can provide consistent illumination, can be light in weight, and can require minimal cooling and/or heating. Where factors such as these are not important considerations, or where there are other countervailing considerations such as spectral or intensity demands that cannot be fulfilled with LEDs, other light sources may be used instead or in addition to an LED. For example, in a system where the illumination source is not to be scanned, such as those discussed elsewhere herein, weight may not be an important consideration and a non-LED source could be used, according to certain embodiments.

The term "LED" or "light emitting diode" is used herein to refer to conventional light-emitting diodes, i.e., inorganic semiconductor diodes that convert applied electrical energy to light. Such conventional LEDs include, for example, aluminum gallium arsenide (AlGaAs), which generally produce red and infrared light, gallium aluminum phosphide, which generally produce green light, gallium arsenide/phosphide (GaAsP), which generally produce red, orange-red, orange, and yellow light, gallium nitride, which generally produce green, pure green (or emerald green), and blue light, gallium phosphide (GaP), which generally produce red, yellow and green light, zinc selenide (ZnSe), which generally produce blue light, indium gallium nitride (InGaN), which generally produce bluish-green and blue light, indium gallium aluminum phosphide, which generally produce orange-red, orange, yellow, and green light, silicon carbide (SiC), which generally produce blue light, diamond, which generally produce ultraviolet light, and silicon (Si), which are under development. LEDs are not limited to narrowband or monochromatic light LEDs; LEDs may also include broad band, multiple band, and generally white light LEDs.

The term LED is also used herein to refer to Organic Light Emitting Diode (OLED), that can be polymer-based or small-molecule-based (organic or inorganic), edge emitting diodes (ELED), Thin Film Electroluminescent Devices (TFELD), Quantum dot based inorganic "organic LEDs," and phosphorescent OLED (PHOLED). As used herein, the terms "excitation source," "irradiation source," and "light source" are used interchangeably.

Thus, according to certain embodiments, the LED can be a standard semiconductor device, an organic LED, or an inorganic LED. Examples of organic LEDs are QDOT-based LEDs and a nanotube-based LEDs. The LED can be a stack of LED's such as a stack of organic LEDs or a stack of organic LED layers.

According to various embodiments, the LED radiation source can contain one LED or an array of individual LEDs. For example, super bright LEDs can be used and can be arranged in a light array. According to various embodiments, separate LEDs or a packaged set of LEDs can be used in an array. According to various embodiments, each LED can be a high power LED that can emit greater than or equal to about 1 mW of excitation energy. In various embodiments, a high power LED can be used that can emit at least about 5 mW of excitation energy. In various embodiments wherein the LED or array of LEDs can emit, for example, at least about 50 mW of excitation energy, a cooling device such as, but not limited to, a heat sink or fan can be used with the LED. Individual or arrays of high-powered LEDs can be used that draw, for example, more than about 10 watts of energy, about 10 watts of energy or less, about five watts of energy or less, or about 3 watts of energy or less. Exemplary individual LED and LED array sources are available, for example, from Stocker Yale (Salem, N.H.) under the trade name LED AREALIGHTS, and from Lumileds Lighting, LLC (San Jose, Calif.) under the trade name Luxeon Star. According to various embodiments, LED light sources can use about 1 microwatt (μW) of power or more, for example, about 5 mW, about 25 mW, about 50 mW, about 1 W, about 5 W, about 50 W, or about 100 W or more, each individually or collectively when used in an array.

As another example, high power red, blue and green emitters in a one-piece package are available from multiple sources as off the shelf items, and other colors are possible in custom-made packages. High power LEDs in the LED package minimize the number of individual or physically separate emitters required to generate the necessary light output. Since each color in multi-element package can be turned on and off separately, using such multi-element packages as a excitation light source can provide wavelength selectivity without extensive filter of the excitation light. Light shaping and homogenizing optics may be used, according to certain embodiments, to match the output of a multi-element package to that of broad band sources and/or to improve illumination uniformity.

According to various embodiments, the light source can include a combination of two, three, or more LEDs, laser diodes, and the like, such as, having a first relatively short wavelength (e.g., UV-blue) LED and a second "redder" or longer wavelength LED. For example, the light source can include an LED that can emit radiation at about 475 nm, an LED that can emit radiation at about 539 nm, and an LED that can emit radiation at about 593 nm.

According to various embodiments, excitation light emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as the focusing lens 106 (FIG. 1), 206 (FIG. 2), and 306 (FIG. 3). The lens can be a collimating lens, for example, a Fresnel lens.

According to various embodiments, organic LEDs (OLEDs), such as quantum dot LEDs can be used. See, e.g., U.S. patent application Ser. Nos. 10/440,920 to Boege (filed May 19, 2003) and 10/440,852 to King (filed May 19, 2003), both incorporated by reference herein. Quantum dots may also be used as optical tags or markers in sample assays.

A quantum dot based LED can emit light in an emission band that is narrower than an emission band of a normal LED, for example, about 50% narrower or about 25% narrower. The emission band of the quantum dots can be a function of the size distribution of the quantum dots, and thus can theoretically be extremely narrow. For example, the quantum dot based LED can be tuned to emit light in a relatively tight emission bandpass, for example, an emission bandpass including a full-width of half-max (FWHM) of about 10 nm or less, about 20 nm or less, or about 50 nm or less. Quantum dots having a range or mix of sizes, composition, or both, can also be used, to provide, for example, generally white light or light of multiple specific wavelengths or wavelength ranges The quantum dot based LED can increase the efficiency of the system. The efficiency of a quantum dot based LED can theoretically be higher than that of conventional LEDs, potentially about 90% or more, for example, approaching 100%, such as when sandwiched directly between two conductive films with each film directly touching each quantum dot as opposed to the present 20% efficiency typical for standard LEDs. Quantum dot based LEDs can be made utilizing a slurry of quantum dots, where current flows through an average of several quantum dots before being emitted as a photon. This conduction through several quantum dots can cause resistive losses in efficiency. Quantum dots can also provide many more colors than conventional LEDs.

OLED films, including, for example, quantum dot based LEDs, can be applied to a thermal block used for heating and cooling samples in a fluorescence system without interfering with the operation of the thermal block. According to various embodiments, an OLED can be used and/or produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement or array. One or more OLEDs can form a shape surrounding, for example, a sample reservoir, a series of sample reservoirs, an array of a plurality of sample reservoirs, or a sample flow path. The sample flow path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, an OLED can be used and can be formed from one or more stable, organic materials. The OLED can be capable of emitting light when a voltage is applied across the organic material. OLDEs can use different electrically conductive films or layers in electrical contact with the organic material to provide the voltage path. At least one of the electrically conductive films can be optically transparent, and may be chosen from, for example, indium tin oxide (ITO), zinc oxide, and carbon nanotube-based layers.

According to certain embodiments, an optical system may include two or more LED scan be used, either simultaneously or sequentially. The use of a plurality of different excitation wavelengths can improve the use and accuracy of the calibration matrix used to distinguish fluorescence emissions of various dyes.

For example, an optical system may include both first and second LEDs configured to provide excitation light to the sample substrate. The multiple LEDs may be similar or identical, to provide, for example, increased intensity or uniformity as compared with a single LED. The multiple LEDs may also be directed to provide excitation light to different areas of the sample substrate.

The multiple LEDs may also be different, for example being configured to provide respectively different wavelength range excitation light. The use of different wavelength ranges may be used to, for example, probe different tags in a sample having (or potentially having) different optical absorption properties. For example, the first LED may have an emission spectrum suitable for the absorption spectrum of a first fluorescent probe and the second LED may have a different emission spectrum corresponding to or suitable for the absorption spectrum of a second fluorescent probe in the sample.

Multiple LEDs can be operated simultaneously, sequentially, or both depending on the application. For example, multiple LEDs can be operated simultaneously to provide enhanced intensity or illumination of multiple areas on the sample substrate. Multiple LEDs can also be operated simultaneously to provide multiple excitation wavelengths, for example, to simultaneously provide excitation light for multiple target probes.

According to certain embodiments, sequential operating of multiple LEDs may be used, for example, to probe multiple target probes and/or sample areas. Sequential operation can thus be used to detect and distinguish among multiple optical signatures with as few as one optical detector. For instance, according to certain embodiments, the detection data from a single optical detector can be synchronized to the sequential operation of the LEDs. For instance, when LED #1 is activated the detection data from the single optical detector will correspond to the probes and areas that LED #1 is configured to illuminate, and when LED #2 is activated (and LED #1 deactivated) the detection data from the same single optical detector will correspond to the probes and areas LED #2 is configured to illuminate.

The use of a plurality of different excitation wavelengths, such as with multiple LEDs, can provide enhancements when used with a calibration matrix used to calibrate an optical system prior to measuring an unknown sample. In this regard, multiple LEDs may also be used with or configured for use without performing an optical calibration of the system. For example, a calibration may entail directing the excitation light from multiple LEDs having multiple distinct optical wavelength ranges onto the sample substrate and measuring an optical response from the sample substrate, such as a sample substrate having a calibration matrix of various dyes.

A calibration may further entail measuring the optical response from the sample substrate with first and second optical detectors, and calibrating the system based at least partially on the measured optical response. The calibration may take into account, for example, the absolute intensity of each measured optical response as well as a ratio of different optical responses. Based on the measured optical response, the calibration could include, for example, a scaling factor for different excitation wavelengths to account their respective intensities as determined using a sample calibration matrix. The calibration could additionally or alternatively include a scaling factor for different excitation and or detection intensities or efficiencies for different areas on the sample substrate. The calibration could additionally or alternatively include a scaling factor to account for variations or changes in the optical response of one or more of the optical detectors. The scaling factor for the calibration may include, for example, a constant term, a first order intensity correction, and/or any higher order correction or scaling factors Passive Thermal Control Systems and Methods According to certain embodiments, there is a passive thermal control system configured to passively control an operating temperature of the TDU. The passive thermal control system may comprise at least one of an insulating oven and a thermally conductive substrate. A passive thermal control system and method may also include active thermal control systems and methods as discussed elsewhere herein.

An insulating oven as part of a passive thermal control system at least partially encompasses the TDU, and is configured to provide some degree of thermal insulation to the TDU. That is, an insulating oven can be configured to provide thermal insulation around a thermally sensitive device or element. In one embodiment, an insulating area may be a thermally insulating box surrounding or partially surrounding the thermally sensitive device or element. The insulation may comprise, for example, polyisocyanate, polyurethane, polystyrene, foamed polymers, gaps comprising air or other low heat conducting gases, and vacuum gaps.

Insulation that can buffer against temperature changes may be used according to certain embodiments. For example, insulation material may comprise a material having a phase transition of, for example, 20° C. Due to the additional energy required to change the phase, e.g., from solid to liquid, the material will effectively buffer against temperature changes at this phase change temperature. In other words, if the material is in equilibrium between two phases at 20° C., additional heat added or removed will not change the temperature of the material until the material has fully transitioned to one of the two phases. These materials are known as "phase change insulation" or insulation containing a "phase change material." Polymeric materials, where the phase change temperatures can be tuned by controlling properties such as chain length and cross-linking, may be suitable for this type of buffering. These buffering materials may also be encapsulated, such as in microspheres, to further control their thermal properties and enhance their handling.

Insulation based on phase change materials has been used in and proposed for use in construction applications, such as in U.S. Pat. Nos. 5,626,936 and 6,645,598 to Alderman, which are incorporated herein by reference. Other phase thermal buffers based on phase change materials are described in U.S. Pat. Nos. 5,290,904 to Colvin, 6,703,127 to Davis, and 6,217,993 to Pause, which are also incorporated herein by reference. According to certain embodiments of the present invention, these materials and systems, and others capable of providing insulation based on a phase change material, may be used to provide thermal insulation. It is believed that the phase change insulation has not been used as part of a temperature compensated optical system, as disclosed herein.

Passive thermal compensation systems may also include thermal conductive substrates designed to conduct thermal energy away from a device in thermal contact therewith. For example, a thermally conductive substrate as part of a passive thermal control system is in thermal contract with the TDU and is configured to conduct thermal energy between the temperature dependent unit and the thermally conductive substrate.

A thermally conductive substrate may also provide a more uniform thermal environment to multiple devices or elements in thermal contact therewith. Depending on the thermal mass (i.e., total heat capacity) of the thermally conductive substrate and elements in thermal contact therewith, a thermally conductive substrate may also act as a thermal buffer for the contacted devices or elements. In such a case, a large thermal mass will minimize changes in temperature with the addition or removal of thermal energy and minimize variations in the temperatures of devices in thermal contact therewith. A thermally conductive substrate may include or be associated with cooling elements, such as cooling fins, to dissipate heat and maintain a more stable thermal environment for the contacted devices and elements.

A passive thermal control system may, according to certain embodiments, comprise an insulating oven and a thermally conductive substrate, as well as optionally other components. It may also comprise, for example, additional components such as heaters, coolers, or fans that are not activated by a thermal control signal. For example, the passive thermal control system may comprise a heat sink with cooling fins in thermal contact with the TDU and a cooling fan directed at the cooling fins of the heat sink, where the cooling fan is active during operation of the system regardless of the TDU temperature. Additionally, as noted elsewhere herein, a passive system may be combined with an active system, such as a fan that is activated or deactivated based on temperature changes.

As still further examples, a cooling system can comprise a heat sink assembly, comprising, for example, a substantially planar base in thermal contact with the TDU and fins extending from the base. According to various aspects, the cooling system can include a fan and/or at least one cooling member configured to control the heat sink temperature. The fan and/or the cooling member can be actively controlled, for example, or can be maintained in a steady state (e.g., on). According to some aspects, the fan and/or the cooling member can be operated to actively hold the heat sink at or near a desired temperature.

According to certain aspects, an additional cooling member can be configured to lower the temperature of the ambient air being directed toward the heat sink by the fan. The cooling member can lower the ambient air temperature by outputting a cooling fluid such as, for example, $CO_2$ (bottled or dry), liquid nitrogen, pressurized air, or the like into the airflow path of the fan.

As further examples, the cooling member can comprise one or more Cold Gun Aircoolant Systems™, such as those marketed by EXAIR®. The Cold Gun uses a vortex tube, such as those marketed by EXAIR®, to convert a supply of compressed air into two low pressure streams—one hot and one cold. The cold air stream can be muffled and discharged through, for example, a flexible hose, which can direct the cold air stream to a point of use, for example, in the path of airflow from the fan to a heated surface such as, for example, the heat sink. Meanwhile, the hot air stream can be muffled and discharged via a hot air exhaust.

The cooling member can also comprise, for example, one or more microchannel cooling loops, such as those marketed by Cooligy (Mountain View, Calif.) for use with high-heat semiconductors. An exemplary cooling loop can comprise a heat collector defined by fine channels, for example, 20 to 100 microns wide each, etched into a small piece of silicon, for example. In some embodiments, the channels can be configured to carry fluid that absorbs heat generated by a heated surface such as, for example, the heat sink. In some embodiments, the cooling loops can be configured to absorb heat from the ambient air in the path of airflow from the fan. The fluid passes a radiator, which transfers heat from the fluid to the air, thus cooling the fluid. The cooled fluid then return to a pump, for example, an electrokinetic pump, where it is pumped in a sealed loop back to the heat collector.

According to various aspects, the cooling member can comprise one or more Cool Chips™, such as those marketed by Cool Chips plc. Cool Chips™ use electrons to carry heat from one side of a vacuum diode to another. As such, Cool Chips™ are an active cooling technology, which can incorporate passive cooling components, such as the fan. A Cool Chip™ layer can be disposed between a heating system and the heat sink to introduce a gap between the heating system and the heat sink. By addition of a voltage bias, electrons can be encouraged to move in a desired direction, for example, from the heating system to the heat sink, while their return to the heating system is deterred by the gap. Thus, the heat sink can be hotter without damaging the heating system. In some aspects, one or more Cool Chips™ can be arranged to absorb heat from ambient air to thereby cool the system.

According to certain embodiments, a passive control system can comprise the thermally conductive substrate, the LED, and the optical detector. According to these embodiments, at least the LED and optical detector are components of the TDU and are in thermal contact with the thermally conductive substrate. The thermally conductive substrate is configured to conduct thermal energy between (i) both LED and the optical detector and (ii) the thermally conductive substrate.

An advantage of embodiments where the LED and the optical detector are in thermal contact with a common thermally conductive substrate is the enlarged thermal mass of the system. This enlarged thermal mass may provide an enhanced degree of thermal stability or compensation to the elements in thermal contact therewith. In embodiments having both active and passive thermal compensation, the active thermal compensation may be in thermal contact with the thermally conductive substrate to provide active temperature control to all elements in thermal contact with the thermally conductive substrate, such as the LED and optical detector.

According to various embodiments, a thermal interface material (TIM) can provide a good thermal contact between two surfaces, for example, between an LED support and a substrate, and/or between an LED housing and a thermoelectric device. The TIM can include silicone-based greases, elastomeric pads, thermally conductive tapes, thermally conductive adhesives, or a combination thereof. Zinc-oxide silicone can be used as a TIM.

A thermal compliant pad TIM is described in U.S. Pat. No. 5,679,457 to Bergerson, which is incorporated herein in its entirety by reference. Commercially available examples of thermal compliant pads include those of Berquist Co. (Chanhassen, Minn.), including their SIL-PAD® and GAP-PAD products, such as GAP PAD VO ULTRA SOFT materials.

According to various embodiments, a TIM can be disposed between a heat-transfer device and an LED. According to certain embodiments, the TIM or thermally compliant pad may have a thermal conductivity in the range of 0.08 to 5 w/m-K, or, as another example, depending on the type, a TIM can have a thermal conductivity in the range of 0.08 to 0.37 W/m-K, 0.33 to 0.82 W/m-K, or 0.9 to 3 W/m-K, such as available from Berquist Co (Chanhassen, Minn.).

For example, according to certain embodiments, a passive control system includes a thermally conductive substrate that includes or is in thermal contact with a thermally compliant pad. The thermally compliant pad, which is also in thermal contact with the TDU, is configured to conduct thermal energy between the TDU and the thermally conductive substrate.

According to various embodiments, a heat conductive adhesive or compliant pad can be used to attain good thermal conductivity between a heat sink or heat source, and other system components, for example, to maintain temperature stability in the system. A heat exchange pathway can be established for system components such as photodiodes and LEDs using a ground path to a common metal or thermally conductive layer or plate as in, for example, a PCB ground plane or other thermally conducting layer, such as a surface or interior highly thermally conductive (e.g., aluminum or steel) layer. The layer or plate can be a metal, for example, aluminum, copper, or other electrically conductive metals. The system can thus maintain temperature stability and keep various system components at substantially the same temperature. The heat exchange pathway can exchange heat with the ground plane or other thermally conductive layer. Other thermal interface materials, for example, adhesive backed resistive elements, can be used to achieve good contact with the system components. For active thermal compensation, a resistive heater can be disposed in or on a common substrate (e.g., attached to the ground plane of a PCB) shared with other electrical circuits included in the system, for example.

According to certain embodiments, thermal insulation can be used to enclose or partially enclose the system components in a thermally isolated environment. The enclosure can have openings allowing, for example, illumination from the LEDs to illuminate a detection zone. The insulation may also be optically transparent to allow light transfer to and/or from the detection zone, and may be, for example, glass or glass plates separated by a vacuum or fill with a gas. Heat exchange pathways can be disposed in the enclosure to allow for thermal transfer between the system and an ambient environment. The heat exchange pathway can be, for example, a vent in the enclosure. A cooling fan can cool the thermally isolated environment provided by the enclosure. The heat exchange pathway can include, as another example, a high conductivity thermal surface included in the enclosure and in thermal contact with a thermoelectric device. The system components can be separated from the enclosure using a thermal insulator to lower a heat exchange rate between the enclosure and the temperature control components. According to certain embodiments, the thermally insulating enclosure may contain components such as the excitation source, a temperature sensor, and/or the temperature regulating system. Known methods of heat transfer include conduction, convection, and thermal radiation.

Example 4

Figure 4:
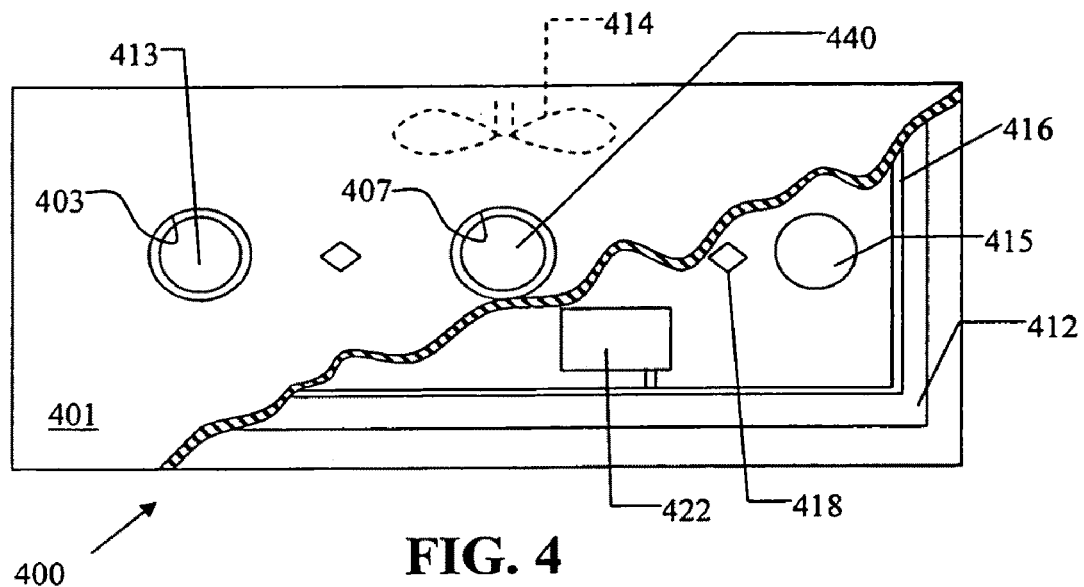
FIG. 4 is a top view in partial cross-section of a system including a fan and heating element providing temperature stabilization for an LED according to various embodiments.

FIG. 4 is a top plan cross-sectional view of a system 400. A housing 401, also known as a cave, an oven, or an enclosure, can include openings such as 403 and 407 as shown. LEDs 413, 415 can irradiate through respective openings (403) to illuminate one or more reaction regions (not shown). The opening 407 can allow transmission or passing of emission beams from a reaction region to a detector 440. One or more temperature sensor 418 can be disposed in or on a housing substrate 412. The substrate 412 can include a heating device 416. The temperature sensor 418 can be disposed on or in the housing substrate 412. LEDs 413 and 415, and detector 440, can be disposed on or in the housing substrate 412. A temperature regulator or temperature regulating system 422, capable of receiving a signal from the temperature sensor 418, can be included, for example, in the housing 412 or can be external to the system. The temperature regulating system 422 can control the heating device 416 and/or a cooling fan 414, as desired, for example, to maintain the system 400 within a desired or pre-set temperature range. The housing 401 can provide a relatively small, thermally isolated, volume to be temperature-regulated by the temperature regulating system 422. Control circuits (not shown) necessary to utilize the LEDs 413, 415 and the detector 440 can be housed within the housing 401. Excitation light can be emitted from the LEDs 413, 415 and directed toward one or more reaction regions. LED 413 can produce excitation light of a different wavelength range than LED 415, for example, LED 413 can produce blue light and LED 415 can produce green light. LED 413 can be operated simultaneously or sequentially with LED 415.

Example 5

Figure 5:
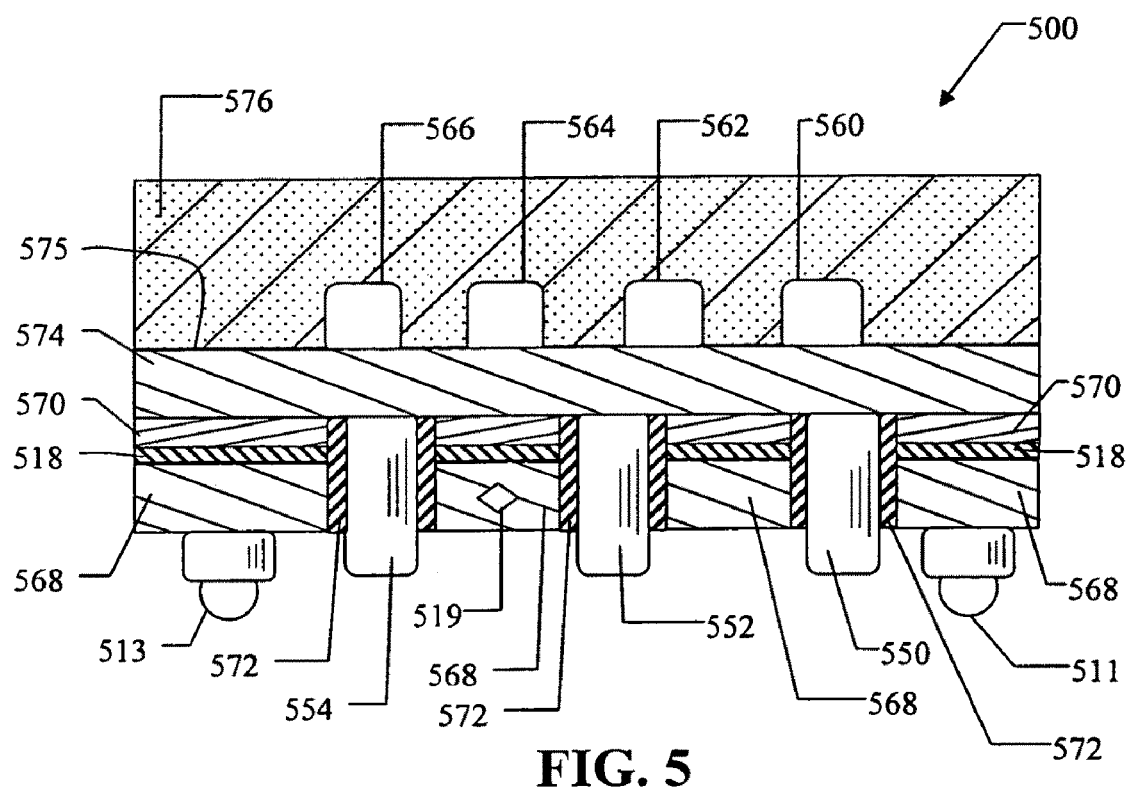
FIG. 5 is a side view in a partial cross-section of a system providing a strong thermal conductive path according to various embodiments.

FIG. 5 is a side cross-sectional view of a system 500 according to various embodiments. The system 500 can include photodiode detectors 550, 552, and 554 disposed on a substrate 574. The substrate 574 can have control circuits 560, 562, 564, and 566 disposed on a first surface or back side 575 thereof. The system 500 can include an LED 513 mounted on a plate 568 having a high thermal conductivity. For example, the plate 568 can comprise aluminum. An elastomer pad 570 having a high thermal conductivity can be disposed between the substrate 574 and the plate 568. The elastomer pad 570 can electrically isolate an electric resistive heater 518 from the substrate 574. The photodiode detectors 550, 552, and 554 can be adhered or bonded or soldered to the substrate 574 using, for example, an adhesive 572. A temperature sensor 519 can be disposed in thermal contact with the system 500, for example, the temperature sensor 519 can be disposed in contact with the plate 568. Thermal insulation 576 can be disposed adjacent the second surface or backside 575 of the substrate 574 to thermally isolate the system 500 from an ambient environment. The system can maintain the control circuits 560, 562, 564, 566, the photodiode detectors 550, 552, 554, and the LEDs 511, 513, at the same temperature. Accordingly, a constant and uniform temperature can be maintained across the system 500.

Optical Configurations, Regulation Systems and Methods

Various embodiments of configurations of LEDs, reaction regions, and intervening devices that can be used to direct excitation light from light sources toward reaction regions, can be found, for example, in co-pending U.S. patent application Ser. No. 10/440,920 entitled "Optical Instrument Including Excitation Source" to Boege et al., co-pending U.S. patent application Ser. No. 10/440,852 entitled "Apparatus And Method For Differentiating Multiple Fluorescence Signals By Excitation Wavelength" to King et al., both filed on May 19, 2003, and U.S. patent application Ser. No. 10/735,339, filed Dec. 12, 2003, Reexamination Control No. 90/007,275, filed, Oct. 29, 2004, for U.S. Pat. No. 6,211,989, all of which are incorporated herein in their entireties by reference.

The LED or the LED array can include a plurality of LEDs mounted on a substrate. The LED can be in thermal contact with a temperature regulating system. The temperature regulating system can control a heat-transfer device and/or a temperature sensor. The temperature regulating system can maintain the operating temperature of the LED such that the operating temperature does not change appreciably. For example, the operating temperature can be maintained such that it does not fluctuate by more than 10 degrees Celsius during operation, for example, by not more than 5 degrees Celsius, by not more than 1 degree Celsius, by not more than 0.5 degrees Celsius, or by not more than 0.1 degree Celsius or less. The temperature regulating system can maintain the operating temperature of the LED such that the operating temperature does not exceed the bounds of a programmed temperature range. According to various embodiments, a temperature regulating system and a temperature sensor can be included in a single-unit or can be included in an integrated device, for example, a MAXIM DS1620 device available from Maxim Integrated Products, Inc. of Sunnyvale, Calif.

The temperature sensor and the LED do not necessarily have to be in physical contact. The temperature regulating system can adjust a monitored temperature of the LED to compensate for any thermal masses intervening between the LED and the temperature sensor and to thus derive, calculate, or estimate an operating temperature.

According to various embodiments, the LED can be cooled to maintain life and illumination uniformity requirements of a system. According to various embodiments, the LED can be cooled subambient to achieve higher brightness. According to various embodiments, a forced air cooling system or a thermoelectric device, for example, a Peltier device, can be used to cool the LED and to keep the LED from exceeding a maximum operating temperature. Additional cooling members, as discussed above, may also be used, according to various embodiments.

According to various embodiments, the temperature of the LED can be monitored optically, for example, with an optical sensor, and thermal characteristics of a system and spectral characteristics of any LEDs embedded within the system, can be recorded. With an understanding of the spectral coefficients of the LED as a function of an operating temperature, the effects of a spectral shift can be mitigated upon detection of optical properties of a sample. According to various embodiments, system calibrations based on a dye matrix or detection data can be altered in accordance with the conditions (e.g., temperature) under which the dye matrix or detection data was gathered or detected. Based on such calibrations and compensations, thermal effects on excitation light emitted by LEDs, including spectral shifts and intensity changes, can be compensated, minimized, or eliminated, as much as possible.

According to various embodiments, the temperature of an LED can be monitored and a computing apparatus can adjust the detection data to compensate for the spectral shifts and/or intensity changes of excitation light emitted from the LED. The compensation for the shifting can be varied across wavelength ranges, for example, different compensations can be provided for different wavelengths of LEDs. A system can be provided that can include a data adjustment unit comprising a memory adapted to store at least two operating temperatures and at least one respective excitation beam characteristic shift for each operating temperature. A plurality of respective excitation beam characteristic shifts can be stored in the memory. The adjustment data can be in the form of a plurality of respective coefficients. Each coefficient can correspond to a respective LED of an LED array. An exemplary range of coefficients can be from about 0.04 nm/° C. to about 4.0 nm/° C., for example, based on deviation from a set or average operating temperature. LEDs with higher and lower temperature coefficient may also be used, consistent with various embodiments of the present invention.

The coefficients can include two or more nominal temperature coefficients corresponding to two or more LEDs. The coefficients can be determined or designated based on the position of a respective LED in an LED array. The spectral shift and temperature coefficients can be different for different temperatures. The spectral shift and temperature coefficients can be calculated, determined empirically, or any combination thereof. During operation, the spectral shift and temperature coefficients can then be obtained, for example, from a look-up table. The table can be sorted by temperature, for example. The table can be provided in a long-term storage of a computer system, for example. Thermal properties of multiple components (e.g., an LED and an optical filter) can be combined to yield a combined thermal coefficient that can then be used to compensate for system-wide (i.e., multiple component) temperature effects. Multiple temperature sensors may also be used to monitor the temperature of multiple components, though multiple temperature sensors may also be used to monitor the temperature of a single component According to various embodiments, optical detection instruments utilizing LEDs can obtain very stable intensity or spectral characteristics by stabilizing an operating temperature of an LED. Illumination stability can be important to minimize the signal noise in the system. Illumination stability can improve the sensitivity of the instrument to detect low concentration dyes. Spectral stability can be used to maintain values for the deconvolution matrix associated with a set of dyes to prevent quantification errors. Similarly, variations in intensity resulting from temperature changes can be different for different wavelengths of LEDs, resulting in apparent spectral instability.

According to various embodiments, illumination stability can be improved by allowing the illumination source to warm-up. According to various embodiments, shutters can block excitation light from reaching a sample to prevent bleach out (photo bleaching). For example, according to various embodiments, shutters can block excitation light from reaching a sample to prevent bleach out during illumination source warm-up. The illumination source can be brought to a desired operating temperature range prior to enabling or turning on the illumination source, using a heater and/or a cooler. Regulating the temperature of the illumination source prior to enabling the illumination source can prevent the need for a shutter and/or can reduce the warm-up time period. According to various embodiments, samples can be subjected to a reaction or a series of reactions, for example, temperature cycled in a nucleic acid sequence amplification or in a sequencing process. According to various embodiments, the shutter can be unblocked in coordination with the reaction or the series of reactions, to detect and collect data at an appropriate time, for example, during a fluorescence detection reading of the sample.

According to various embodiments, laboratory instrumentation utilizing a relatively more robust dye matrix can be less susceptible to the spectral shift of an LED, such as thermally-based spectral shifts, than a system with a relatively less robust dye matrix. The AB 7500 system available from Applied Biosystems of Foster City, Calif., can have a very good dye matrix and can have little susceptibility to spectral shift for at least most dyes.

According to various embodiments, an operating temperature of an LED (as an exemplary temperature dependent component) can be controlled with a Peltier-effect thermoelectric device, a heat pump, an electrical resistance heating element (Joule heater), fluid-flow through channels in a metal block, reservoirs of fluid at different temperatures, tempered air impingement, a combination thereof, or the like. According to various embodiments, the thermal device can include a fan to direct air-flow over cooling fins, or a cold bar to assist in a heat transfer between an LED and another thermal mass, such as air. According to various embodiments, the thermal conductivity of the LED and/or a platform supporting the LED can be greater than that of a surrounding ambient environment, for example, the surrounding air.

According to various embodiments, a thermoelectric device can be used as a heat-transfer device, for example, an XLT module available from Marlow Industries, Inc. of Dallas, Tex. Controls for the thermoelectric device can include an adjustable-bipolar DC output current power supply. The power supply can provide programmable PID control/ramp to set point control, deviation alarms, and automatic and manual operating modes. In reactions, for example, real-time monitoring of Polymerase Chain Reaction (PCR) reactions, thermoelectric devices can both heat and cool, as desired, the LED by using a bi-directional or bi-polar power supply under programmable and/or logic control. The programmable and logic control can be provided by using a general purpose computer, or custom built hardware, for example, a field programmable gate array (FPGA) or micro controller. Thermoelectric devices can be specifically designed to withstand the continuous temperature excursions required in PCR use.

According to various embodiments, a heat-transfer device can include a vapor-cycle device, for example, a Freon-based (or other refrigerant) vapor compression or absorption refrigerator. In such units, thermal energy can be extracted from a region, thereby reducing its temperature, then rejected to a "heat sink" region of higher temperature. Vapor-cycle devices can include moving mechanical parts and can include a working fluid, while thermoelectric elements can be totally solid state.

Example 6

According to certain embodiments, the present invention provides an optical system comprising a sample substrate, an LED, first optical detector and optionally one or more additional (e.g., a second) optical detector(s), an excitation-emission selector, and an emission selector. Such systems may, of course, include the active and passive thermal control systems and components discussed elsewhere herein.

For example, there can be at least one LED configured to provide excitation light to a sample substrate, such as to a sample well. The excitation light can be provided by way of an excitation-emission selector (e.g., FIG. 8, element 616) or without such a component, as in FIG. 1. As just one possibility, the excitation-emission selector may be a interference element (e.g. dichroic) configured to receive the excitation light at an approximately 45 degree angle, relative to an axis normal to the receiving surface of the dichroic. The interference element can be configured to reflect, in this case also at a 45 degree angle, excitation light towards the sample substrate. The excitation-emission selector could also be a beam splitter, and such a beam splitter could similarly be configured for approximately 45 degree angles of incidence and reflection. Some excitation light may pass through the excitation-emission selector, and this stray light could be contained in a light trap as discussed elsewhere herein. Additional elements, such as mirrors and lenses, may be used between the LED and the excitation-emission selector and/or between the excitation-emission selector and the sample substrate to, for example, turn or shape the excitation light along a desired light path.

The central wavelength of the excitation light can be, for example, about 470 nm. First and second optical detectors can be configured to receive emission light, by way of the excitation-emission selector, from the sample substrate and generate detection data. Additional optical detectors, such as a third optical detector, may also be included according to certain embodiments.

As just one possibility, consistent with the illustrative example above of configuring the excitation-emission selector at a 45 degree angle relative to the exciation light received from the LED, the excitation-emission selector can be configured to receive emission light from the sample substrate at an approximately 45 degree angle and transmit some or all of this emission light such that it is directed towards the optical detectors.

Thus, the excitation-emission selector can be configured to provide at least two functions: (1) direct the excitation light received from the LED towards the sample substrate and (2) direct the emission light received from the sample substrate towards the optical detectors.

In the optical path from the excitation-emission selector towards optical detectors, one or more emission selectors, can be configured to receive the emission light from the excitation-emission selector and to selectively direct (i) a first optically distinct range of the emission light to the first optical detector and (ii) a second optically distinct range of the emission light to the second optical detector. According to certain embodiments, additional emission selectors may be used to further separate out sub-ranges of emission light and direct them to respectively different optical detectors. Mirrors may also be used according to certain embodiments to control the optical path of light in the system, including the path of the emission light to one or more optical detectors, such as by folding beams to obtain a compact footprint.

For example, a first emission selector may be configured to receive, at a 45 degree angle of incidence relative to its surface normal, emission light from the excitation-emission selector and reflect a first optically distinct range from the emission light towards the first optical detector. The emission selector may be, for example, an interference element configured to reflect, at a 45 degree angle, the first optically distinct range. Emission light not reflected (or otherwise lost due to, for example, absorption) by the first emission selector can pass through the first emission selector towards the second optical detector. Having selectively removed an first optically distinct range of light from the emission light, the transmitted light will necessarily be a second optically distinct range, which can be directed to a second optical detector via, for example, a mirror. Additional optically selective emission filters can be added to further separate the emission light into more optically distinct ranges.

Other configurations would include the use of beam splitters to separate out multiple portions of the emission light, each have the same (or nearly the same) optical properties, with the possible exception of intensity, which may be regulated by the type of beam splitter (e.g., 50:50, 75:25) used. Thus, a first beam splitter could be configured to receive emission light from the excitation-emission selector, direct (via reflection, for example) a fraction of the intensity towards a first optical detector and direct (via transmission, for example) the remaining intensity towards other optical detectors, such as a second optical detector. A filter can then be used in front of each optical detector to selectively direct or pass an optically distinct ranges of light to each optical detector. Such filters can also be used in conjunction with optical detectors even where a selective emission selector is used to further prevent unwanted ranges of light from reaching the detector.

In the case of either an optically selective emission selector or a non-selective element used to direct emission light towards detectors, other optical elements, such as lenses and mirrors, may also be used. For example, one or more lenses can be used in the optical path between the emission selector or beam splitter and the optical detector to focus emission light towards an optical detector. As another example, a mirror can be used to fold or otherwise redirect the optical path.

As used herein, first and second "optically distinct ranges" of light refers two ranges of light distinct from one another based on at least one spectral property. For example, first and second optically distinct ranges may have two different central wavelengths, e.g., 520 and 555 nm, as in the case of fluorescent emission from fluorophores FAM and VIC. As another example, first and second optically distinct ranges may have two different ranges between points of full-width at half-maximum (FWHM) amplitude, such as a first range from 500 to 550 nm and a second range from 590 to 630 nm, to distinguish between fluorophores FAM and ROX. Optically distinct ranges may, however, have some common features, such as partially overlapping spectra. Thus, as one example, a first optical spectral range from 515 to 565 nm would be considered optically distinct from a second spectra range of from 555 to 595 nm.

An optical system may also include one or more lenses, such as optional lenses discussed above in the optical path to the optical detector(s). As another example, a system may include one or more lenses configured to focus the excitation light towards the sample substrate. As another example, a system may include one or more lenses configured to substantially collimate the emission light and direct the substantially collimated emission light to the excitation-emission selector and/or the emission selector. Collimation can be desirable, for instance, to provide better wavelength selectivity for an interference filter.

As yet another example, a system may include one or more lenses configured to both focus excitation light towards the sample substrate and collect the emission light from the sample substrate. For example, an objective lens (which may contain more than one lens) may be used to both focus excitation towards a sample and collect emission light from the sample. As a further example, the lens may also collimate the emission light while directing it towards the excitation-emission selector.

The excitation and emission light may pass through additional components between the optical head and the sample substrate. For example, a cover plate may be used to seal the wells of the sample substrate. The cover plate may be heated to control or maintain a temperature in the wells. Additionally, the sample substrate may be or include a thermal cycler block to further control reaction conditions, such as to control thermal cycling for PCR.

A system may, according to certain embodiments, also include optical filters, such as on optical filter to prevent stray excitation light from reaching the optical detectors. For instance, such a filter may be located in the optical path between the excitation-emission selector and the one or more optical detectors. As one example, an optical filter can be a 513 nm long pass filter to effectively block 470 nm excitation light but still pass longer wavelength emission light. As also discussed above, an optical filter may also be used in close proximity to an optical detector to prevent unwanted light ranges from reaching that detector. For example, the optical filter may be a narrow bandpass filter tuned or set to a particular fluorescent emission wavelength range. An optical filter may also be used to select or reject a particular range of light from the LED.

One or more of the LED and optical detectors may be mounted on a common support. The common support may be a thermally conductive substrate and/or a PCB. The support may include control electronics, such as for power and signal processing. Control and processing electronics may also be located in a separate unit, such as in a computer processor. A thermal interface material (TIM) to provide heat conduction between the LED and optical detectors and the support may also be used.

According to certain embodiments, the optical system may also include a thermal compensation system with a TDU that includes at least one of the LED and the first and second optical detectors. The thermal compensation system may also comprise an active temperature compensation system, a passive temperature control system, or both.

According to certain embodiments, the excitation-emission selector and the emission selector (collectively "optical selectors") may be selective or non-selective. In the case of a selective excitation-emission selector, it may be configured to selectively direct the excitation light received from the LED towards the sample substrate and selectively direct the emission light received from the sample substrate towards the optical detector. Similarly, a selective emission selector may be configured to selectively direct a first optically distinct range of emission light to a first optical detector and a second optically distinct range of emission light to a second optical detector. "Selective" and "selectively" as used herein with respect to optical elements used to selectively direct or separate different optical wavelengths or wavelength ranges does not necessarily entail 100% selectivity but only requires a preferential discrimination between different optical wavelengths, wavelength ranges, or other optical properties (e.g., polarization). An Example of a non-selective excitation-emission selectors or emission selectors would be a beam splitter (e.g., a 50:50 beam splitter). A beam splitter used as an excitation-emission selector could be configured to direct at least a portion the excitation light received from the LED towards the sample substrate and to direct at least a portion of the emission light received from the sample substrate towards the optical detectors. A beam splitter used as an emission selector could be configured to direct a portion of received emission light to a first optical detector and another portion having the same spectral range to a second optical detector. Optical selectors may each independently comprise at least one of an interference (e.g., dichroic), dispersive, beam splitting, filtering, and diffractive optical elements. For example, diffractive optical selectors may be chosen from, for instance, gratings (e.g., transmission and reflection gratings) and holographic reflectors.

Functionally, optical selectors can be configured to, according to certain embodiments, select a given wavelength or wavelength range from a broader range or combination of wavelengths. For example, the excitation-emission selector can be configured to selectively reflect at, for instance, a 45° angle of incidence, excitation light in order to direct the excitation light from the light source (LED) towards the sample. Optical selectors, such as interference filters, may be used at other angles as well, depending on the design and properties of the optical selector. Similarly, other optical selectors, such as beam splitters and absorptive filters, may be used at angles other than 45°, including both steeper and shallower angles of incidence. The excitation-emission selector can also be configured to selectively pass an emission light wavelength or wavelength range, in order to selectively direct emission light from the sample toward an optical detector. The emission selector, for example, can be configured to pass a first wavelength range to a first optical detector and a second wavelength range to a second optical detector.

According to certain embodiments the excitation-emission selector may comprise at least one interference (e.g., dichroic) optical element configured to selectively reflect one of the excitation light and the emission light and selectively transmit the other of the excitation light and the emission light. As another example, the emission selector may comprise at least one interference (e.g., dichroic) optical element configured to selectively reflect the first optically distinct emission range and selectively transmit the second optically distinct emission range.

The optical selectors, such as an emission selector, may also contain, according to certain embodiments, a dispersive element such as a prism or grating. For example, a dispersive element may be configured to disperse the received emission light, and to selectively direct the first optically distinct portion of the emission light to a first optical detector and direct a second optically distinct portion of the emission light to the second optical detector. According to certain embodiments, the first and second optical detectors can be elements of a common multi-element array detector, while according to other embodiments the first and second optical detectors can be individual optical detectors, such as two photodiodes.

According to certain embodiments, an optical selector may comprise a tunable optical selection element, such as a rotating filter wheel or other tunable filter, such as a birefringent tunable filter. Exemplary filter wheels are disclosed in U.S. Pat. No. 5,784,152 to Heffelfinger, which is hereby incorporated by reference in its entirety. ColorSelect® from Color-Link, Inc. (Boulder, Colo.) is another example of a tunable filter, in particular a birefringent tunable filter, suitable for use in various embodiments.

According to certain embodiments, an optical system according to the present invention may include a rotating emission filter wheel comprising at least two optical filters, an index feature associated with the optical filters, an index position sensor configured to detect an angular position of the rotating emission filter wheel, and a motor configured to rotate the rotating emission filter wheel. For example, there may be at least three optical filters. As another example, there may be five or more optical filters. For example, according to certain embodiments, the rotating emission filter wheel can be configured to selectively and sequentially direct at least five different wavelength ranges of emission light received from the sample substrate to the optical detector. The optical filter wheel could be configured to operate at different speeds, such as a position-to-position time (including settling) of from 10 msec to 2 sec, such as from 10 msec to 0.1 sec.

According to certain embodiments, a rotating filter wheel can be used as an emission selector to simultaneous process multiple distinct emission wavelength ranges. Thus, for example, a first optical filter can be configured to selectively direct (via reflection, for example) a first selected wavelength range of emission light received from the sample substrate to the first optical detector and to selectively direct (via transmission, for example) a second selected wavelength range of the emission light received from the sample substrate to the second optical detector. Additional optical filters on the filter wheel can similarly be configured to simultaneously direct two distinct wavelength ranges, one by, for example, reflection, and the other by, for example, transmission.

According to certain embodiments, an optical system may also include a selective optical component, such as a tunable filter or monochromator, optically located between the LED and the sample substrate configured to selectively direct a desired wavelength range of the excitation light towards the sample substrate. Such a selective optical component, functionally, selectively blocking or passing respectively different wavelength ranges in order to stop unwanted excitation light from being directed towards the detectors such components are not limited to a traditional filters (e.g., long pass, band pass, short pass), but may include other optical components capable providing the desired function. According to certain embodiments it may include diffractive components and polarization dependent components, by way of example.

A component is said to be "optically between" two other optical components (e.g., first and second optical components) when the light path between the first and second optical components passes through or off of (e.g., reflect) the optical component in question. Thus, an optical component need not be physically between two other components to be "optically between" these components.

According to certain embodiments an optical system may also include a light trap configured to trap stray excitation light not directed towards the sample substrate. The light trap can be located, for example, to trap stray excitation light passing through an excitation-emission selector. The light trap may include optically absorbing materials, baffles, or both to prevent the light from escaping out of the trap.

The light trap may also comprise additional elements, such as a light detector configured to monitor at least one optical property of the stray excitation light. For example, it could monitor total intensity or intensity of a given wavelength or wavelength range, such as when coupled with a filter (e.g., bandpass filter). Thus, according to certain embodiments, an optical detector in a light trap (or elsewhere in the beam path) may function as a temperature sensor to monitor a temperature dependent optical property (e.g., intensity or spectrum) of the excitation source. An advantage of this configuration is that the excitation light intensity can be monitored without interfering with or detracting from the light intended to illuminate the sample substrate.

Low Mass Scan Heads and Scanning Methods

An optical system according to certain embodiments includes a low mass scan head. As used herein, a "low mass scan head" is understood to mean a unit configured to scan relative to a sample substrate, where the unit has a low inertial mass such that scanning can occur at a relatively fast rate. According to certain embodiments, a low mass scan head may entail a scan head having a relatively low mass and/or configured for a relatively high velocity and/or acceleration. "Low mass" scan heads are further understood to refer to scan heads containing a reduced number of components such that its mass is comparatively reduced. The additional components may be included, for example, in an associated fixed optical head.

For example, a conventional optical head, where both the light source (LED) and the detector are scanned, has a mass of 2,200 grams and an acceleration of 3.2 m/sec$^2$. In comparison, a low mass system using the same components but where the optical detector is in a fixed head, the light source (LED) is in a scanned low mass scan head, and the fixed and scanned optical heads are connected via an optical fiber, the low mass scan head mass is 800 grams and has an acceleration of 8.8 m/sec$^2$. As a further comparison, a low mass system using the same components but where the optical detector and light source (LED) are both in the fixed head and the scanned low mass optical head is connected via an optical fiber to the fixed optical head, the low mass scan head mass is 500 grams and has an acceleration of 14 m/sec$^2$.

A low mass scan head may provide other benefits and features, such as, for example, reduced instrument shaking during scanning based on the lower mass being scanned, the shorter scan time enabled by greater acceleration or velocity, or any combination thereof. Further, low mass scan heads may be actuated with smaller motors and drive trains, all of which contribute to a reduced overall instrument footprint and potentially reduced cost as well.

According to certain embodiments, a low mass scan head may include the proximal end of at least one optical fiber. The low mass scan head can be configured to provide one or more functions, including scanning relative to the sample substrate, directing excitation light towards the sample substrate, collecting emission light from the sample substrate, and directing the emission light to the optical fiber proximal end. The optical fiber, having distal and proximal ends, can be configured to conduct emission light from its proximal to its distal end.

According to certain embodiments, an optical system may also include a fixed optical head. The fixed optical head does not need to be configured for scanning relative to the sample substrate. Thus, it can be maintained in a fixed position and its mass does not affect any relative scanning rate.

The fixed optical head can include, for example, the distal end of the optical fiber and one or more optical detectors, such as the first and second optical detectors. Functionally, according to such embodiments, the fixed optical head can be configured to direct the emission light from the distal end of the optical fiber and towards the optical detectors.

Multiple scan heads may also be used. For example, there may be multiple pairs of fixed and scanning optical heads. Each pair may be configured, for example, to detect distinct optical signatures by, for example, having different excitation sources or having emission selectors configured to select different emission wavelengths. Pairs of optical scanning heads may also be configured optically the same or similar to each other, and be configured to scan different locations on the sample substrate to, for example, increase the overall scanning rate. There may also be multiple scanning optical heads associated with a single fixed optical head, and conversely there may be multiple fixed optical heads associated with a singe scanning optical head.

Example 7

Figure 6:
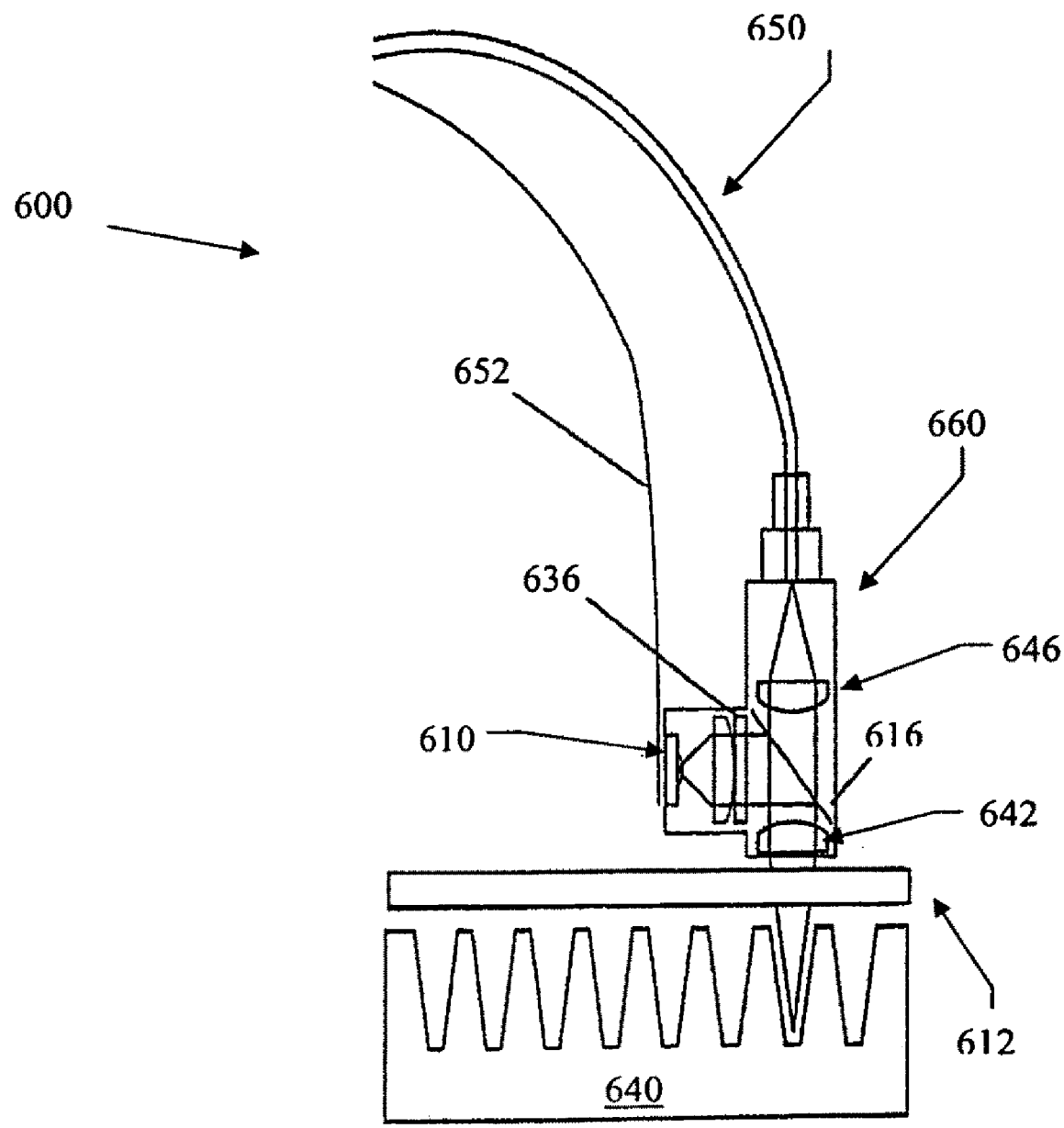
FIG. 6 is a side view in a partial cross-section of a first low mass scan head system according to various embodiments.

For low mass scan head configurations according to some embodiments, an excitation source can be located in either a low mass scan head or a fixed optical head, or both if multiple excitation sources are used. For example, a low mass scan head can include the LED. The low mass scan head can also include the excitation-emission selector. An exemplary low mass scan head system 600 where the low mass scan head includes both an LED 610 and an excitation-emission selector 616 is illustrated in FIG. 6.

The system includes a fixed optical head (not shown) and a scanning optical head 660. The optical heads are optically connected via optical fiber 650, which may be a single optical fiber or bundle of optical fibers. Emission light is focused into the proximal end of optical fiber 650 via lens 646. Emission light emerging from the distal end of optical fiber 650 into the fixed optical head can be collimated, for example via one or more lenses before being directed to on or more detectors, as discussed elsewhere herein. The LED 610 can be electronically controlled, for example, to a stationary PCB board or control and reading device via electrical connection 652.

Electrical connection 652 can be used for other functions as well, such as operating a thermal control system, if present, or transmitting a signal from a temperature sensor, if present. Optics for the selection and detection of the emission light in fixed optical head can be configured as, for example, discussed herein for the emission light subsequent to the excitation-emission selector.

In operation, light emitted from LED 610 can be collimated by a lens, pass though a filter 636 to narrow the emission wavelength on route to excitation-emission selector 616. The excitation-emission selector 616 can reflect at least some of the excitation light toward the sample substrate 640, the excitation light being focused by lens 642 and passing through cover plate 612. Emission light from the sample substrate 640 can be collected with lens 642 and directed to pass through the excitation-emission selector 616, before being focused by lens 646 into the proximal end of the optical fiber 650, on route to the fixed optical head.

Example 8

For low mass scan head configurations according to certain embodiments, the fixed optical head may include the LED or other excitation source. The fixed optical head containing the LED can be configured to direct the excitation light into the distal end of an optical fiber. According to these embodiments, the optical fiber can be configured to direct the excitation light from its distal to its proximal end, and the low mass scan head (which includes the proximal end) can be configured to direct the excitation light from the optical fiber proximal end towards the sample substrate.

Figure 7:
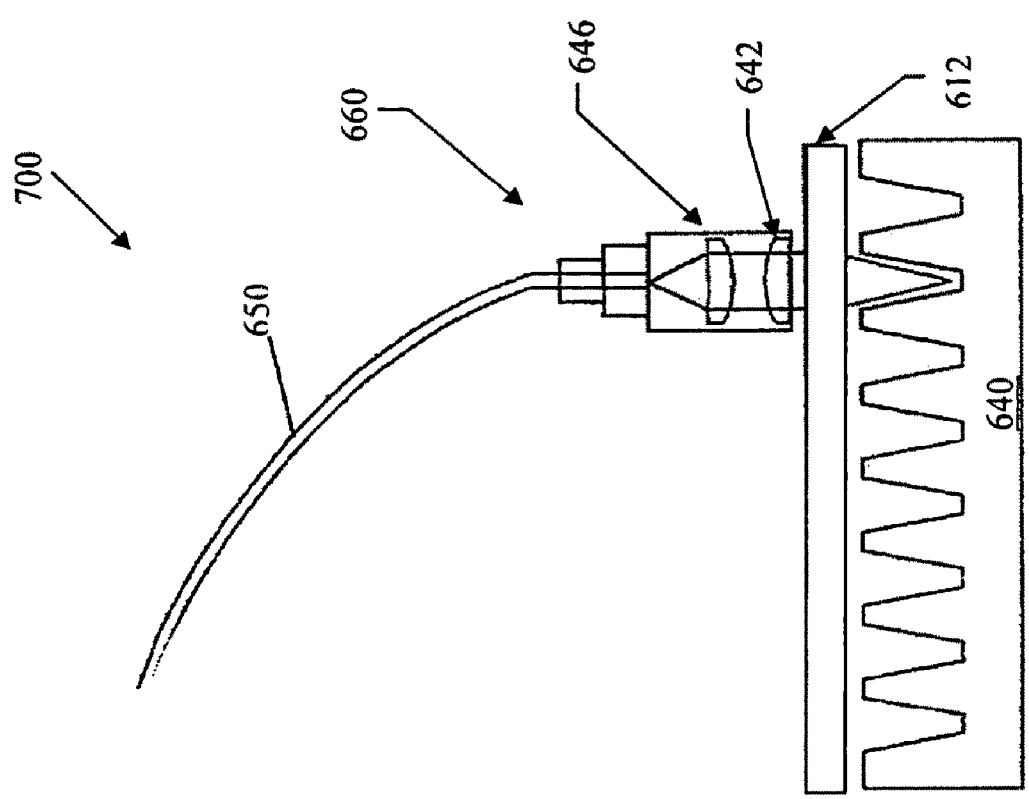
FIG. 7 is a side view in a partial cross-section of a second low mass scan head system according to various embodiments.

As illustrated in FIG. 7, there can be a low mass scan head system 700 where the fixed optical head (not shown) includes at least one LED and optical detectors, and other optional components (e.g., optical, electronic, and/or thermal components). According to certain embodiments where the excitation source is in the fixed head, alternate excitation sources, such as white light sources (e.g., halogen lamps) and narrow band sources (e.g., lasers), may be used instead of or in addition to LEDs. Excitation light from the fixed optical head is focused, such as via one or more lens, into the distal end of the optical fiber 650. The excitation light exiting out of the proximal end of the fiber 650 is collected and collimated with lens 646 and focused towards the sample with lens 642. Lens 642 also collects and collimates emission light from the sample, and lens 646 then focuses the emission light into optical fiber 650 for transmission back to the detector(s) in the fixed optical head.

Example 9

According to certain embodiments, there is an optical system having a detector assembly or fixed optical head that includes a dispersive spectrometer configured to measure spectral properties of the collected emission light. Such a dispersive spectrometer may include, for example, a dispersive element configured to spatially disperse the spectral components of the collected emission light. A dispersive spectrometer may also include one or more detectors, such as, for example, an array detector configured to concurrently measure a range of the spectrally dispersed emission light. As another example, a dispersive spectrometer may include a selection element, such as a moveable slit or mirror, to sequentially direct different spectral components of the dispersed emission light onto detector.

Figure 8:
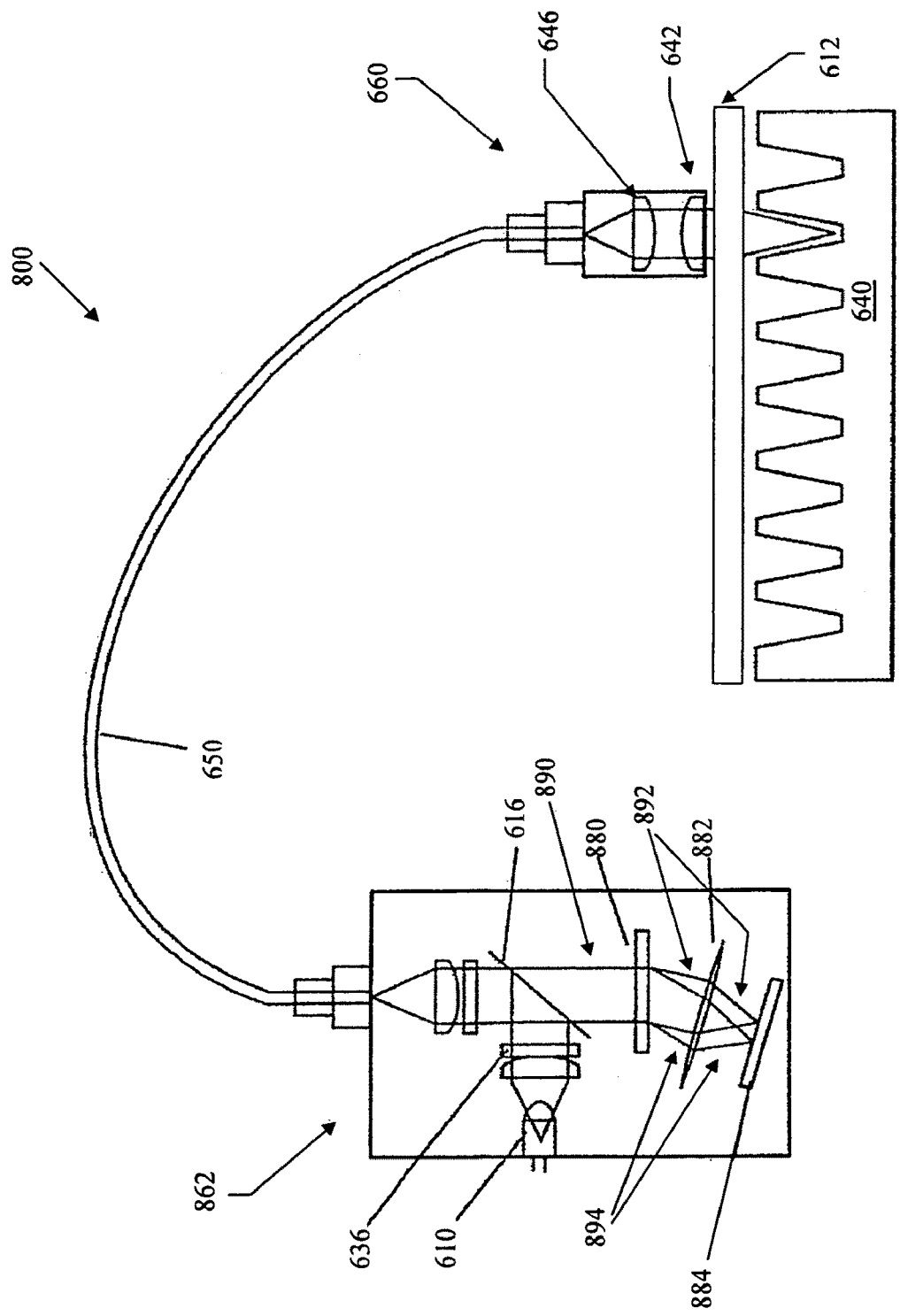
FIG. 8 is a side view in a partial cross-section of a third low mass scan head system having a dispersive spectrometer according to various embodiments.

One illustrative embodiment of a detector assembly dispersive spectrometer is provided in FIG. 8. The illustrated embodiment shows the exemplary dispersive spectrometer components 880, 882, 884 and the excitation source 610 in the fixed optical head, but this is not required according to all embodiments of systems and methods according to the present invention. For example, both the dispersive spectrometer and the excitation source can be included in a scanned optical head. As another example, a dispersive spectrometer can be in a fixed optical head with the excitation source in a scanning optical head.

As schematically shown in FIG. 8 for optical system 800, the dispersive spectrometer includes dispersion element 880, such as a transmission diffraction grating, which is configured to receive emission light 890 and disperse it into multiple spectrally distinct components 892, 894. Reflection gratings and refractive elements, e.g. prisms, could also be used as dispersion elements according to certain embodiments. Focusing lens 882 focuses the spectrally dispersed emission light 892, 894 onto different locations on a multi-element optical detector 884.

Scanning Configurations and Methods

According to various embodiments, scanning of optics relative to the sample substrate can be performed in order to sequentially interrogate multiple locations, such as multiple sample wells, on the sample substrate. According to certain embodiments, scanning may be accomplished with relative linear X and Y translations. According to certain embodiments, scanning may entail relative angular motions. According to certain embodiments, scanning may entail a combination of relative angular and linear motions.

In this context, a relative motion is understood to mean that at least one of the optics and sample substrate are moved such that their position relative to each other changes. For example, a relative motion between or scan of optics relative to a sample surface may entail movement of the optics, with the sample remaining in a spatially fixed position. It may also entail movement of the sample, with the optics remaining in a spatially fixed position. As another example, it may entail combined motions of both the optics and the sample.

For example, according to certain embodiments, scanning may be accomplished by a relative linear motion and a relative angular motion about a rotational axis generally perpendicular to a surface of the sample substrate. In this context, generally perpendicular means that functionally, the scan head will remain sufficiently equidistant from the plane of the surface such that refocusing of the scan head optics is not necessary due to the rotational movement. Thus, while according to certain embodiments rotational axes may be aligned wholly perpendicular to a sample plane, according to certain embodiments some deviation from perpendicular is allowed so long that the scan head optics can still provide the desired function.

According to certain embodiments, the rotary axis can be used to align the optical system with the first row of sample. The linear axis can be moved to scan over the first row of the sample. The linear scanning can be, for example, at a constant speed. The rotary axis will typically remain fixed during the linear scan, but may be adjusted to optimize the optical alignment of the optics relative to the sample. After the first row is completed, the rotary axis aligns for the next row of samples and then holds its position. As before, the linear axis can be scanned, and the process repeated until the sample has been fully interrogated. As one alternative, both linear and angular motions may be used simultaneously to scan the surface.

A scan cycle can begin at a time, for example, $T_o$, and can end with a final time $T_f$. The period of time for a cycle to complete can vary depending on a number of factors including, but not limited to, the number of wells in the set, for example 96; the time required to position each well of the set under the detector; the time required to detect and measure a signal from the spectrally distinguishable species in each well; the time required to move from one well to the next well; and the time for a reaction in a well to occur. According to some aspects, the run time of a reaction can be reduced by calibrating the temperature of each well at the same time that the signal from the spectrally distinguishable species is measured. This temperature calibration can reduce the run time of the reaction while not affecting the data integrity.

According to certain embodiments, the period of time between measuring a signal from a first well to a second well can be less than about 30 seconds, for example less than about 20 seconds, and as a further example, less than about 5 seconds. Once a signal from each well of the set has been measured then another cycle can begin.

Over the course of the cycle, the temperature can increase and/or decrease. For example, each well of a set of multiple wells can have the same temperature, such as 60° C., when the signal from spectrally distinguishable species is measured in a first cycle. After the signal from each well has been measured, the temperature can be increased to, for example, a denaturing temperature, and then decreased. However, for each subsequent cycle, the signal from each well of the set can be read at the same temperature as in the first cycle. For example, if all of the wells during a first cycle are at about 60° C., then all of the well should be at about 60° C. for each subsequent cycle when the signals are read so that the data is not compromised.

In various aspects, including certain PCR applications, for example, well #1 of the set can have a first temperature when its signal is measured. The first temperature can be greater than or equal to an annealing temperature of DNA. The temperature of the thermal cycler block 1 can be slowly increased, and optionally held for a period of time, so that well #2 of the set has a higher temperature when its signal is measured as compared to well #1. In another embodiment, the temperature can be slowly increased in a linear relationship over time, for example, so that one temperature is not held for a period of time. In some aspects, the temperature can range from about 60° C. to about 95° C. over the course of a cycle. For example, well #1 can have a temperature of about 60° C. and well #2 can have a temperature of about 61° C. during a first cycle. For each subsequent cycle, the temperature of the thermal cycler block can be calibrated so that well #1 again has a temperature of about 60° C. and well #2 can have a temperature of about 61° C. The particular temperature of each well is not important for the first cycle, so long as during each subsequent cycle the temperature of each well is substantially the same as it was during the first cycle. Variations in scan speed can be compensated or accounted for in various ways, such as according to U.S. Pat. No. 6,040,586 to Tor Slettnes, incorporated herein by reference.

Example 10

Figure 9A:
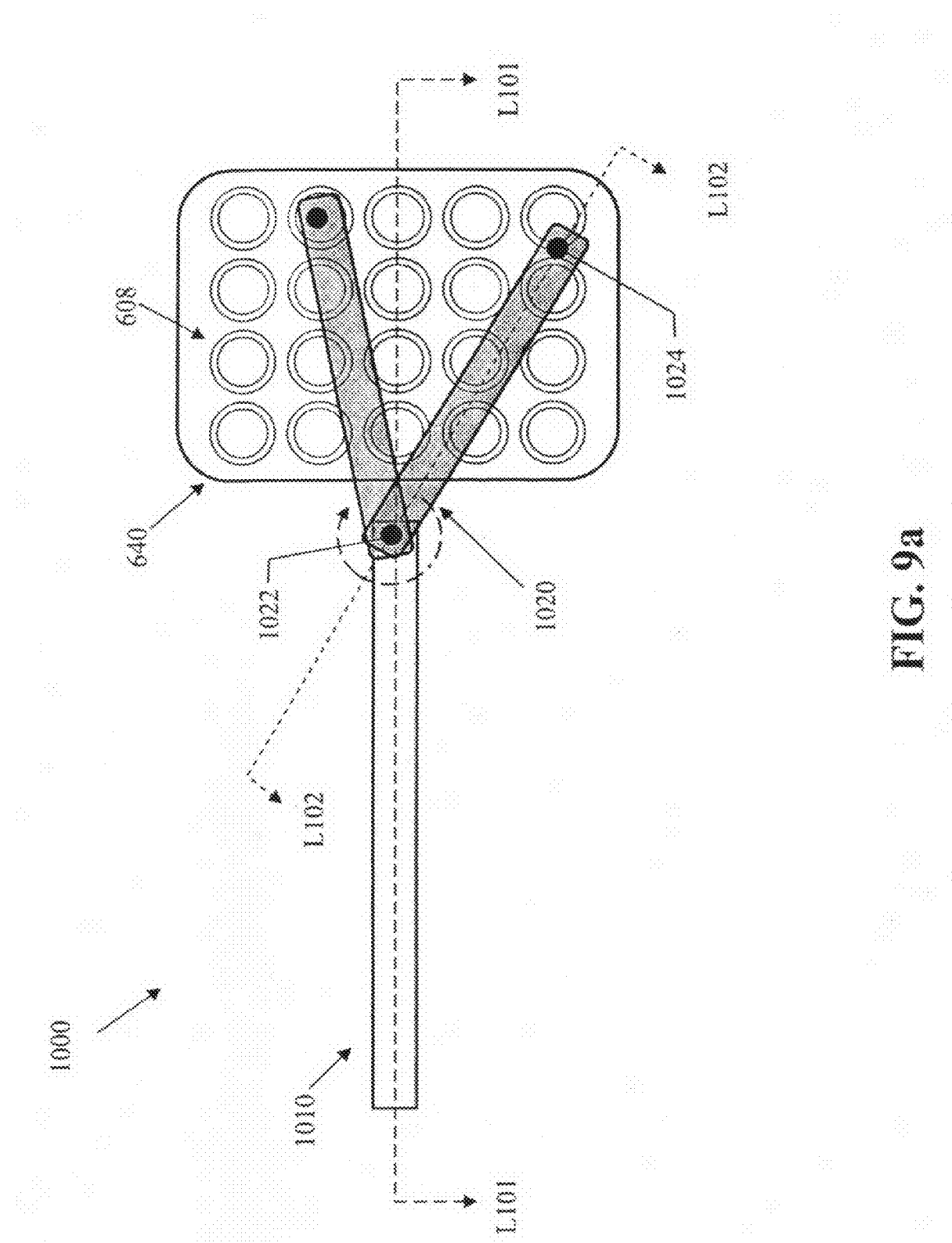
FIG. 9 illustrates embodiments for scanning of 2-dimensional surface using one linear actuator and one rotation actuator, in top views (a, b) and side view cross section (c).
Figure 9B:
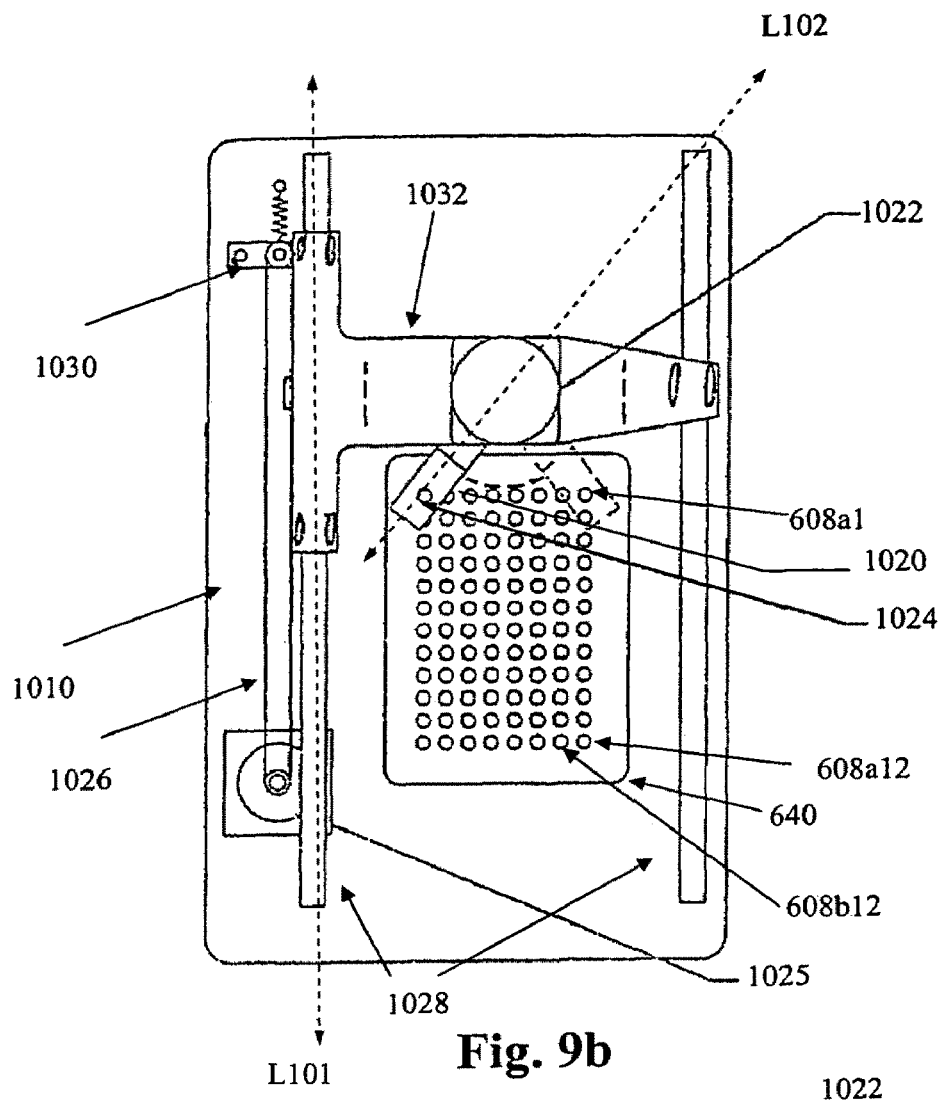
Figure 9C:
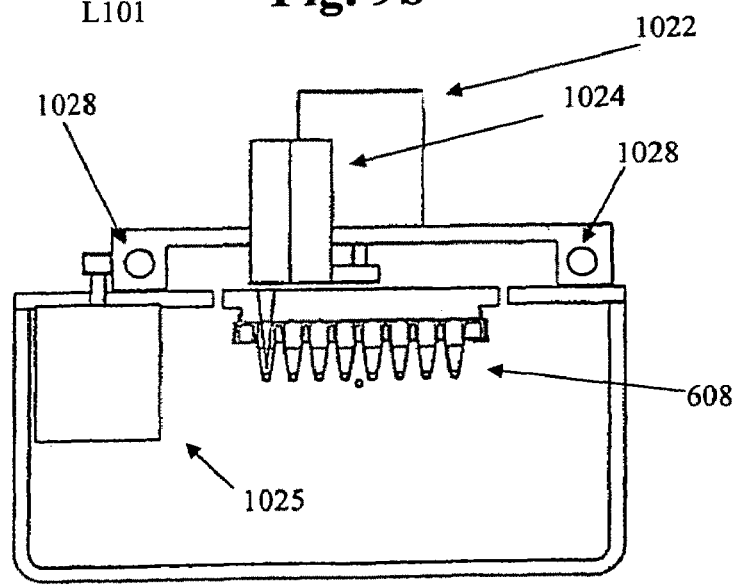

As shown in FIG. 9, a 2-dimensional surface may be effectively scanned by combining a rotation about a single rotational axis with a linear axis scan. In FIG. 9a, the illustrated scanner has a rotation arm 1020 with an axis L102. The rotation arm 1020 is attached to the linear scanner 1010 via a rotational actuator 1022. The linear scanner 1010 in configured to scan a single linear axis L101. As shown, the rotational actuator 1022 rotates about the axis perpendicular to the plane of the paper about the center of the actuator 1022, such that it is generally perpendicular to the plane of the sample. By combining rotational motions of rotational actuator 1022 with linear motions along axis L101 of linear scanner 1010, any location, in particular any sample well 608, on the sample substrate 640 may be interrogated with the optical system 1024. For the purpose of illustration, rotational arm 1020 is shown in two different positions. Additionally, according to certain configurations, there may be multiple rotational arms and rotational actuators, each having at least one associated optical system, with each arm configured to scan the substrate.

According to certain embodiments, the optical system 1024 can be, for example, an LED-based scan head, with or without thermal compensation, as discussed herein. Thus, for example, it may be a low mass scan head, as also discussed herein.

As shown in FIGS. 9b, c, the linear actuator 1010 can be a composed of, among other things, a stepper motor 1025 and a belt drive 1026. The stepper motor actuator can be, for example, a NEMA 17 actuator. The belt 1026 connects between the stepper motor 1025 and a spring-based idler take-up arm 1030. When the actuator 1025 is actuated, platform 1032, which is operably connected to belt drive 1026, is translated parallel to axis L101, while traveling on bushings 1028, which can be bronze, plastic, or other functionally suitable material. The rotational actuator 1022 is mounted on platform 1032, and is also translated parallel to axis L101. The rotational actuator 1022, which can also be, for example, a NEMA 17 actuator, rotates about its central axis, causing arm 1020 and optical system 1024 to sweep out or be aligned to various wells 608 on substrate 640. As the rotational actuator 1022 is adjusted, the longitudinal axis L102 of arm 1020 will be moved to different angles relative to linear axis L101, though remaining in common plane for 2-dimensional scanning of substrate 640.

Thus, for example, combined linear and rotational adjustments can be used to position optical head 1024 about well 608a1. The linear axis can then be scanned, such that the wells a1-a12 are scanned. Combined linear and rotational adjustments can then be used to position optical head 1024 above well 608b12, and then sample row b can be scanned by scanning the linear axis.

Example 11

According to certain embodiments, scanning may be accomplished by two relative angular motions about two respectively different rotational axes generally perpendicular to the surface of the sample substrate. The scanner includes two rotary axis scanners to move the optics across a 2-dimensional surface. For example, a first rotary axis (the "shoulder" rotation) is mounted to an instrument base. A second rotary axis (the "elbow" rotation) is mounted to an arm connected to the first rotary axis. According to certain embodiments, one or both of the rotary axis scanners can be direct drive actuators, and gear and pulley systems can thus be avoided. Coordination of both rotary motions can achieve linear scanning or point-to-point motions.

Figure 10A:
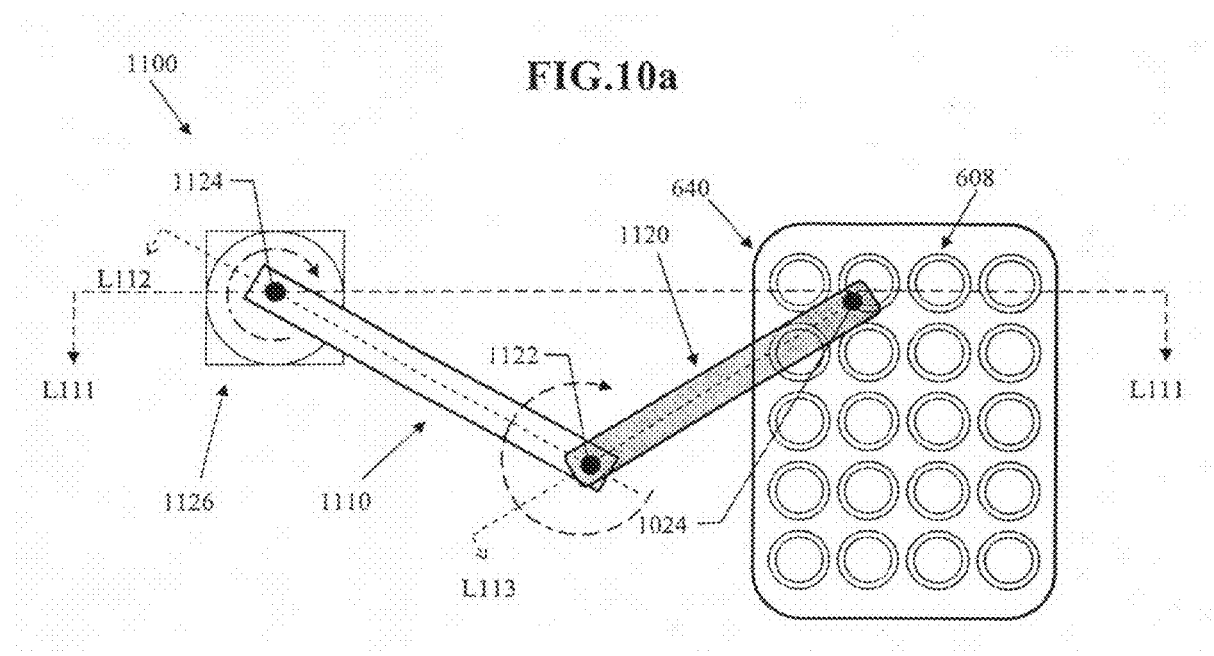
FIG. 10 illustrates embodiments for scanning of 2-dimensional surface using two rotation actuators, in top views (a, b) and side view cross section (c).
Figure 10C:
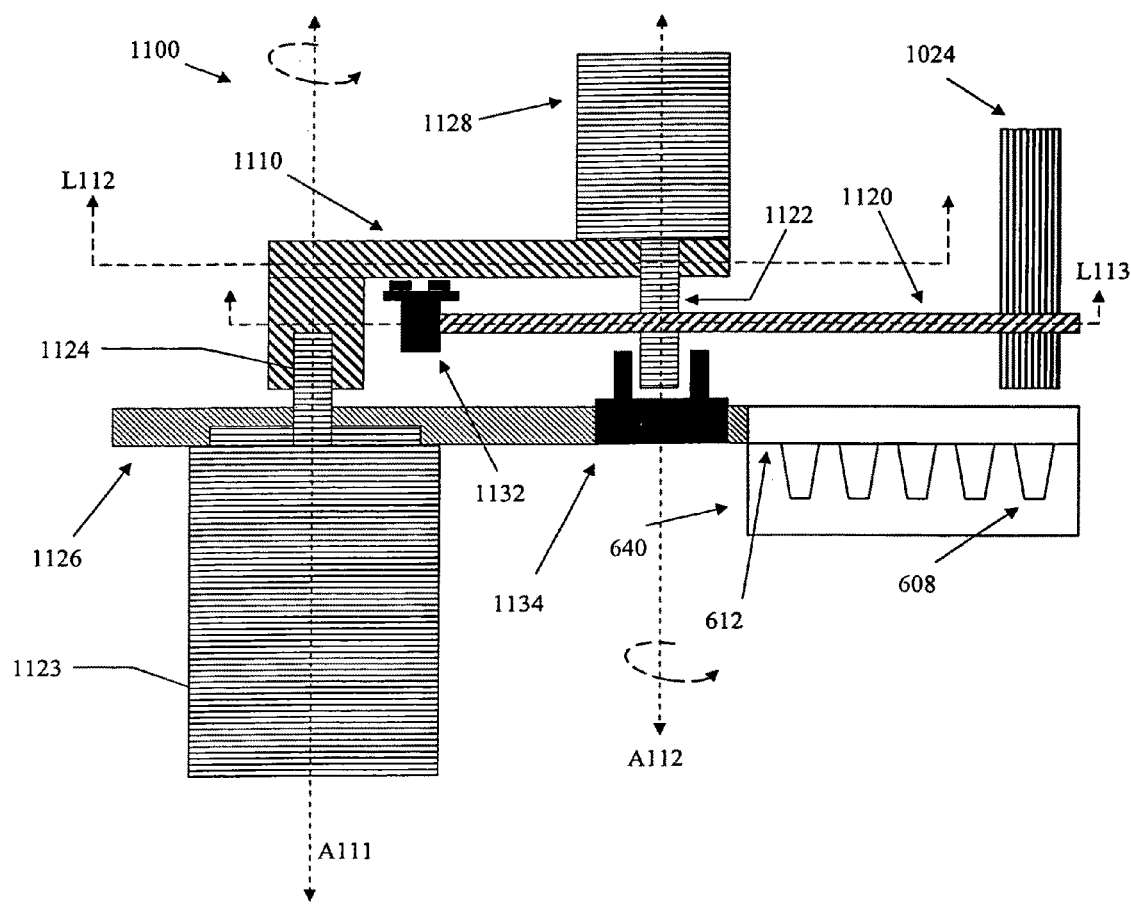

For example, as shown in FIG. 10, there is a first rotary (shoulder) axis and shoulder actuator 1123 with actuator shaft 1124 having one end of an arm 1110 (shoulder arm) connected thereto. The shoulder actuator 1123 is fixed to a base 1126, and is configured to rotate its actuator shaft 1124 about its central axis A111 as shown in FIG. 10c, and perpendicular to the plane of the page for FIGS. 10a, b. The longitudinal axis L112 of the associated shoulder arm 1110 is connected to the shoulder actuator rotational shaft 1124 such that it can be rotated parallel to the plane of the page for FIGS. 10a,b. As shown in FIG. 10b, the longitudinal axis L112 of shoulder arm 1110 can scan or be set to various angles, such as 25.3°, 42.4°, and 61.3° relative to reference line L111.

Attached to the second end of the shoulder arm 1110 is a second rotary (elbow) axis and elbow actuator 1128 with elbow actuator shaft 1122, having one end of arm 1120 ("elbow arm") connected thereto. The elbow actuator 1128 is connected to the second end of the shoulder arm 1110 and is configured to rotate its shaft 1122 about its central axis A112 as shown in FIG. 10c, and perpendicular to the plane of the page for FIGS. 10a,b. The longitudinal axis L113 of the elbow arm 1120 is connected to the elbow actuator 1122 such that it can be rotated parallel to the plane of the page for FIGS. 10a,b. As shown in FIG. 10b, the elbow arm 1120 longitudinal axis L113 can scan or be set to various angles (e.g., 86.6°, 92.2°, and 86.6°) relative to the shoulder arm 1110 longitudinal axis L112. The rotational motions can be coordinated to achieve rectilinear scanning, point-to-point scanning, or any other scanning or motion across the 2-dimensional sample substrate.

As shown in FIG. 10c, the scanning system can also include home position switches or sensors, such as a home position sensor 1132 for the elbow actuator and elbow arm and a home position sensor 1134 for the shoulder actuator and shoulder arm. These, or other tracking or monitoring devices, can be used to track the position the scan head relative to the surface.

For example, prior to conducting a scan, the scan head can move to or though the home position. The position of the scan head after subsequent motions (such as scanning relative to the sample substrate), such as by actuating a linear or rotation actuator, can be referenced to the home position such that the position of the scan head can be tracked. Thus, as a rotational actuator rotates the scan head, the position may be tracked by the number of steps specified by a stepper motor rotary actuator and the geometry of the system. Of course, additional position sensors may be used as well or instead, such as position sensors (e.g., rotary encoders) integrated in an actuator. As another example, tracking the scan head position relative to the sample substrate can be accomplished based (in whole or in part) on a system calibration, which can be calculated prior to the scan, that correlates scan time (or other parameter) with scan position.

Based on the tracked (including subsequently calculated) position of the scan head, detection data can be correlated to the various regions on the surface, such as the various sample wells, in order to correlate and assign the detection data to each sample well. Calibration can also take into account other factors, such as a phase lag of an actuator relative to a control signal.

Example 12

Although various scanning routines are possible, one exemplary scanning routine would be rectilinear scanning. For instance, the combination of a high duty cycle linear scanning combined with a low duty cycle rotational adjustment could be used for efficient rectilinear scanning. As another example, rectilinear scanning can be accomplished with two generally perpendicular linear scanners.

As an example of rectilinear scanning with a high duty cycle linear scanning combined with a low duty cycle rotational adjustment, as shown in FIG. 9, the scanner could be configured to begin at well 608a1 (i.e., column a, row 1) by a preliminary adjustment of the rotational actuator 1022 and the linear actuator 1010. The scanner could then be configured to linearly scan the wells parallel to L101 to the end of the column, i.e., well 608a12, as depicted. The linear scan could be maintained at a constant speed, for example. The rotational arm 1020 could then be adjusted with rotational actuator 1022 to align optical system 1024 with the center of the wells in column b, and held to this angular position. Scanning could then begin with well 608b12 to the first well in that column. The scan could then continue in a similar manner up and down the remaining columns of wells. At the beginning or end of each column, the linear position of platform 1032 may need linear adjustment parallel to L101 to optimize the alignment of the optical system 1024 with the first or last well in the column by accounting for sine variations due to changes in theta.

Example 13

As another example, scanning could be effectuated in a point-by-point manner. For example, the scan head could be aligned over a first sample well and the sample well optically interrogated. Then scan head would then be aligned over a second sample well, with the cycle repeated until all desired sample wells have been interrogated. Such point-by-point can be, according to certain embodiments, accomplished with relatively fast moves of the scan head from one position to the next together with relatively slow movement, or even a specified dwell time with no movement, over each well for interrogation. According to certain embodiments, the point-by-point can entail generally continuous motion of the scan head relative to the surface.

As an example of point-by-point scanning, coordination of both rotary motions of the two axis rotary scanner can achieve linear scanning or point-to-point motions. For example, as shown in FIG. 11b, an end of elbow arm 1120, which can contain detection optics 1024, is shown in three different positions over three different samples wells 608, based on combinations of angles from the shoulder 1124 and elbow 1122 rotary axes. As shown, when the first rotary axis is at 25.3° and the second rotary axis is at 86.6°, a first well can be interrogated. When the first rotary axis is at 42.4° and the second rotary axis is at 92.2°, a second well can be interrogated. Similarly, when the first rotary axis is at 61.3° and the second rotary axis is at 86.6°, a third well can be interrogated.

Other embodiments will be apparent to those skilled in the art from consideration of the present specification and practice of various embodiments disclosed herein. It is intended that the present specification and examples be considered as exemplary only.

What is claimed is:

1. An optical system, comprising:
   a) a sample substrate having a surface, the surface defining a 2-dimensional sample plane;
   b) an excitation source configured to provide excitation light to the sample substrate;
   c) an optical detector configured to receive emission light from the sample substrate and generate detection data;
   d) a scan head configured at least (i) to direct the excitation light towards the sample substrate, (ii) to receive emission light from the sample substrate and direct the emission light towards the optical detector, and (iii) for scanning relative to the sample substrate; and
   e) at least one actuator configured to scan the scan head relative to the sample substrate,
   the at least one actuator being configured to provide at least one of (1) a relative linear motion and a relative angular motion about a rotational axis generally perpendicular to the sample plane and (2) two relative angular motions about two respectively different rotational axes generally perpendicular to the sample plane.

2. An optical system according to claim 1, wherein the system is configured for rectilinear scanning of the scan head relative to the sample substrate surface.

3. An optical system according to claim 1, wherein the system is configured for point-by-point scanning of the scan head relative to the sample substrate surface.

4. An optical system according to claim 1, wherein the optical detector comprises first and second optical detectors configured to receive the emission light from the sample substrate and generate the detection data
wherein the first optical detector is configured to receive a first optically distinct range of the emission light and the second optical detector is configured to receive a second optically distinct range of the emission light.

5. An optical system according to claim 1, wherein the excitation source comprises the first and second LEDs, the first and second LEDs being configured to provide respectively optically distinct ranges of excitation light.

6. An optical system according to claim 1, wherein the scanning comprises the relative linear motion and the relative angular motion, the at least one actuator comprising
a linear actuator having a linear travel axis aligned generally parallel to the sample plane and configured to provide linear movement of the scan head relative to the sample substrate along the linear travel axis;
a rotary actuator having a fixed base and a shaft configured for rotation about a rotational axis aligned generally perpendicular to the sample plane, wherein the fixed base is connected to the linear actuator; and
a first arm having a longitudinal axis, a first end, and a second end, wherein the first end is connected to the rotational actuator shaft and the second end is connected to the scan head; the first arm being configured for rotation of its longitudinal axis generally perpendicularly about the rotational axis.

7. An optical system according to claim 6, further comprising
at least one bushing aligned parallel to the linear travel axis; and
a platform connected to the linear actuator and configured to travel along the at least one bushing, wherein the fixed base of the rotary axis is connected to the platform.

8. An optical system according to claim 1, wherein the scanning comprises the two relative angular motions, the at least one actuator comprising
a first rotary actuator having a fixed base and a shaft configured for rotation about a first rotational axis aligned generally perpendicular to the sample plane;
a second rotary actuator having a fixed base and a shaft configured for rotation about a second rotational axis aligned generally perpendicular to the sample plane, wherein the second rotational axis is aligned generally parallel to the first rotational axis;
a first arm having a longitudinal axis, a first end, and a second end, wherein the first end is connected to the first rotational actuator shaft and the second end is connected to the second rotational actuator fixed base; the first arm being configured for rotation of its longitudinal axis generally perpendicularly about the first rotational axis; and
a second arm having a longitudinal axis, a first end, and a second end, wherein the first end is connected to the second rotational actuator shaft and the second end is connected to the scan head; the second arm being configured for rotation of its longitudinal axis generally perpendicularly about the second rotation axis.

9. An optical system according to claim 1, further comprising
at least one optical fiber having distal and proximal ends, wherein the at least one optical fiber is configured to conduct the emission light from its proximal to its distal end; and
a fixed optical head comprising the distal end of the optical fiber and the optical detector, wherein the fixed optical head is configured to direct the emission light from the distal end of the optical fiber towards the optical detector, wherein
the scan head is a low mass scan head comprising the proximal end of the at least one optical fiber and further configured to direct the emission light to the distal end of the at least one optical fiber.

10. An optical system according to claim 9, wherein the low mass scan head further comprises an LED as the excitation source.

11. An optical system according to claim 9, wherein the fixed optical head comprises the excitation source and is configured to direct the excitation light into the distal end of the at least one optical fiber, the optical fiber is configured to direct the excitation light from its distal to its proximal end, and the low mass scan head is configured to direct the excitation light from the proximal end of the optical fiber towards the sample substrate.

12. An optical system according to claim 9, wherein the fixed optical head comprises a dispersive spectrometer comprising a dispersive element and an array detector or multiple optical detectors configured to measure spectral properties of the collected emission light.

13. An optical system according to claim 9, comprising
an LED as the excitation source;
a thermal control system comprising a temperature dependent unit comprising at least one of the LED and the optical detector; and at least one of
(1) an active temperature compensation system comprising
a temperature sensor configured to (i) monitor at least one temperature dependent property of the temperature dependent unit, and (ii) generate a thermal control signal related to the at least one temperature dependent property, and
an active temperature compensation system configured to receive the thermal control signal and regulate at least one of (i) an operating temperature of the temperature dependent unit and (ii) the detection data from the optical detector to form temperature compensated detection data, wherein the regulation is based at least partially on the thermal control signal, and
(2) a passive temperature compensation system comprising at least one of
(i) an insulating oven at least partially encompassing the temperature dependent unit, and
(ii) a thermally conductive substrate in thermal contact with the temperature dependent unit and configured to conduct thermal energy between the temperature dependent unit and the thermally conductive substrate.

14. An optical system according to claim 9, comprising
an LED as the excitation source;
a thermal control system comprising a temperature dependent unit comprising at least one of the LED and the optical detector; and an active temperature compensation system comprising
- a temperature sensor configured to (i) monitor at least one temperature dependent property of the temperature dependent unit, and (ii) generate a thermal control signal related to the at least one temperature dependent property, and
- an active temperature compensation system configured to receive the thermal control signal and regulate at least one of (i) an operating temperature of the temperature dependent unit and (ii) the detection data from the optical detector to form temperature compensated detection data, wherein the regulation is based at least partially on the thermal control signal.

15. An optical system according to claim 9, comprising an LED as the excitation source;
a thermal control system comprising a temperature dependent unit comprising at least one of the LED and the optical detector; and
a passive temperature compensation system comprising at least one of
  (i) an insulating oven at least partially encompassing the temperature dependent unit, and
  (ii) a thermally conductive substrate in thermal contact with the temperature dependent unit and configured to conduct thermal energy between the temperature dependent unit and the thermally conductive substrate.

16. An optical system according to claim 13, wherein the at least one temperature dependent property comprises at least one of a temperature, a temperature dependent optical property, a temperature dependent electronic property of the temperature dependent unit or the temperature sensor, or any combination thereof.

17. An optical system according to claim 13, wherein the temperature dependent unit comprises the temperature sensor.

18. An optical system according to claim 13, wherein the temperature sensor is in thermal contact with the temperature dependent unit.

19. An optical system according to claim 13, wherein the temperature sensor is configured to monitor at least one temperature dependent optical property of the temperature dependent unit.

20. A method for conducting a scanned optically transduced assay, comprising
   a) using an optical system according to claim 1,
   b) directing excitation light from the scan bead to the sample substrate,
   c) receiving with the optical detector emission light from the sample substrate, and generating detection data based on the received emission light,
   d) scanning the scan head relative to the sample substrate, the scanning comprising at least one of (1) a relative linear motion and a relative angular motion about a rotational axis generally perpendicular to the sample plane and (2) two relative angular motions about two respectively different rotational axes generally perpendicular to the sample plane;
   e) tracking a position of the scan head relative to the substrate, and
   f) correlating the detection data with the position of the scan head.

21. The optical system of claim 1, wherein the at least one actuator comprises a plurality of actuators, and the scan head comprises a plurality of scan heads.

22. The method of claim 20, wherein the at least one actuator comprises a plurality of actuators, and the scan head comprises a plurality of scan heads.

* * * * *